United States Patent
Zerhusen et al.

(10) Patent No.: US 10,377,966 B2
(45) Date of Patent: *Aug. 13, 2019

(54) PARTICULATE LAUNDRY SOFTENING WASH ADDITIVE

(71) Applicant: The Procter & Gamble Company, Cincinnati, OH (US)

(72) Inventors: Jaden S. Zerhusen, Florence, KY (US); Lenae V. Johnson, Cincinnati, OH (US); Alessandro Corona, III, Mason, OH (US); Rajan K. Panandiker, West Chester, OH (US); Michael P. Fontaine, Springboro, OH (US); Charles L. Schmitt, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 83 days.

This patent is subject to a terminal disclaimer.

(21) Appl. No.: 15/828,549

(22) Filed: Dec. 1, 2017

(65) Prior Publication Data
US 2019/0169533 A1    Jun. 6, 2019

(51) Int. Cl.
| | | |
|---|---|---|
| *C11D 3/37* | (2006.01) |
| *C11D 1/62* | (2006.01) |
| *C07C 211/63* | (2006.01) |
| *C08B 11/08* | (2006.01) |
| *C11D 1/12* | (2006.01) |
| *C11D 1/66* | (2006.01) |
| *C11D 1/04* | (2006.01) |

(Continued)

(52) U.S. Cl.
CPC .............. *C11D 1/62* (2013.01); *C07C 211/63* (2013.01); *C08B 11/08* (2013.01); *C11D 1/04* (2013.01); *C11D 1/12* (2013.01); *C11D 1/662* (2013.01); *C11D 3/001* (2013.01); *C11D 3/227* (2013.01); *C11D 3/3707* (2013.01); *C11D 17/06* (2013.01)

(58) Field of Classification Search
CPC ....... C11D 11/0017; C11D 3/001; C11D 1/62; C11D 17/0039; C11D 3/222; C11D 17/06
See application file for complete search history.

(56) References Cited

U.S. PATENT DOCUMENTS

| 4,237,016 A | 12/1980 | Rudkin et al. |
| 6,492,322 B1 | 12/2002 | Cooper et al. |

(Continued)

FOREIGN PATENT DOCUMENTS

| EP | 0002085 A3 | 6/1979 |
| EP | 0385529 A3 | 5/1991 |

(Continued)

OTHER PUBLICATIONS

U.S. Appl. No. 15/828,513, filed Dec. 1, 2017, Zerhusen et al.
(Continued)

*Primary Examiner* — John R Hardee
(74) *Attorney, Agent, or Firm* — Gary J. Foose

(57) ABSTRACT

A composition including a plurality of particles, the particles including about 25% to about 94% by weight a water soluble carrier; about 5% to about 45% by weight a quaternary ammonium compound; about 1% to about 40% by weight a fatty acid; and about 0.5% to about 10% by weight a cationic polymer; wherein each of the particles has a mass from about 1 mg to about 1 g.

20 Claims, 2 Drawing Sheets

(51) Int. Cl.
*C11D 3/00* (2006.01)
*C11D 3/22* (2006.01)
*C11D 17/06* (2006.01)

(56) References Cited

U.S. PATENT DOCUMENTS

| | | |
|---|---|---|
| 7,871,976 B1 | 1/2011 | Aouad |
| 8,476,219 B2 | 7/2013 | Aouad |
| 2005/0020476 A1 | 1/2005 | Wahl |
| 2006/0217288 A1 | 9/2006 | Wahl |
| 2008/0014393 A1 | 1/2008 | Denome et al. |
| 2008/0079993 A1 | 4/2008 | Kanamoto |
| 2008/0242584 A1 | 10/2008 | Wahl |
| 2009/0042766 A1* | 2/2009 | Mayer ............... C11D 3/001 510/516 |
| 2012/0030882 A1* | 2/2012 | Wetrosky ............ C11D 1/62 8/137 |
| 2014/0179587 A1 | 6/2014 | Brown et al. |
| 2016/0010033 A1* | 1/2016 | Tan .................. C11D 3/046 510/356 |
| 2016/0122693 A1 | 5/2016 | Sodd |
| 2016/0369211 A1 | 12/2016 | Dykstra et al. |
| 2017/0342346 A1 | 11/2017 | Zhang et al. |
| 2017/0349865 A1 | 12/2017 | Zerhusen et al. |
| 2018/0079993 A1 | 3/2018 | Zhang et al. |
| 2018/0371378 A1* | 12/2018 | Danzer ............... C11D 3/505 |

FOREIGN PATENT DOCUMENTS

| | | |
|---|---|---|
| EP | 1502942 A1 | 2/2005 |
| EP | 3158038 B1 | 3/2019 |
| WO | WO9323510 A1 | 11/1993 |
| WO | WO2008009521 A1 | 1/2008 |
| WO | WO2013036662 A1 | 3/2013 |
| WO | WO2016078941 A1 | 5/2016 |
| WO | WO2016078942 A1 | 5/2016 |
| WO | WO2016101980 A1 | 6/2016 |
| WO | WO2016102527 A1 | 6/2016 |
| WO | WO2016135217 A1 | 9/2016 |
| WO | WO2018055107 A1 | 3/2018 |
| WO | WO2018055121 A1 | 3/2018 |

OTHER PUBLICATIONS

U.S. Appl. No. 15/828,524, filed Dec. 1, 2017, Zerhusen et al.
U.S. Appl. No. 15/828,536, filed Dec. 1, 2017, Zerhusen et al.
U.S. Appl. No. 15/828,562, filed Dec. 1, 2017, Zerhusen et al.
All Office Actions for U.S. Appl. No. 15/828,513.
All Office Actions for U.S. Appl. No. 15/828,536.
U.S. Appl. No. 16/203,911, filed Nov. 29, 2018, Zerhusen et al.
Corrigan, O.I., et al.—Dissolution Properties of Polyethylene Glycols and Polyethylene Glycol-Drug Systems International Journal of Pharmaceutics, vol. 4, No. 1—Nov. 1, 1979, pp. 67-74.
International Search Report for International Application No. PCT/US2018/062936, dated Mar. 8, 2019, 20 pages.
XP-002788248—Polyethyleneglycol 9000 (PEG 9000) flakes_powder, SRL Product Datasheet and Specifications, www.srlchem.com/products/product_datasheet/productId/142433/Polyethyleneglycol-9000—PEG-9000, retrieved Jan. 22, 2019, 1 page.
XP-002788249—Polyethylene Glycol 3350 ExiPlus, www.srlchem.com/products/product_datasheet/productId/143688/Polyethylene-Glycol-3350-Exi-Plus, retrieved Jan. 22, 2019, page.
XP-002788270—Polyethyleneglycol 2000 for synthesis www.merckmillipore.com/Nllen/product/polyethylene-glycol-2000,MDA,CHEM-821037, retrieved on Jan. 22, 2019, 3 pages.
XP-002789158—Ester Quaternary for Fabric Softener, www.scribd.com/document/392592125/SUNJIN-Surfactant-Catalogue-Fabric_Softener, retrieved Feb. 21, 2019, 4 pages.

* cited by examiner

US 10,377,966 B2

PARTICULATE LAUNDRY SOFTENING WASH ADDITIVE

FIELD OF THE INVENTION

Through the wash laundry softening additive.

BACKGROUND OF THE INVENTION

Consumers continually express interest is products that can simplify the processes they use to launder clothes, help them reduce the amount of time they spend dealing with dirty laundry, and help them achieve high levels of cleanliness and softness for their family's clothing. Cleaning and softening of laundry presently requires consumers to dose two products to either different compartments of the washing machine or to dose one product to the washing machine and one product to the dyer.

The process of laundering fabric can be broken up into three basic steps: washing, rinsing, and drying. The washing step typically employs water and detergent composition comprising anionic surfactant, along with other active agents that are compatible with anionic surfactants in the unused product form and in the wash liquor formed during the washing step. After washing, the laundry is rinsed one or more times as part of the rinsing step.

Presently, laundry softening is most often and practically accomplished during the rinsing step with a liquid softening composition that is separate from the detergent composition or during the drying step. To apply liquid softening composition to the laundry in the washing machine, the liquid softening composition is introduced to the laundry during the rinsing step. The liquid softening composition may be automatically introduced into the rinse from a compartment that keeps the liquid softening composition separate from the washing composition. The compartment may be part of the agitator, if present, or another part of the washing machine that can be opened to dispense the liquid softening composition into the drum. This is often referred to as softening through the rinse. Softening through the rinse requires the consumer to dose the detergent composition and the softening composition to different locations of the washing machine, which is inconvenient.

Laundry softening can also be accomplished during the drying step using fabric softening sheets. With either of these approaches to cleaning and softening, cleaning is performed separately from softening.

Consumers find it inconvenient to have to dispense multiple products to different locations, whether the locations are part of the washing machine or the locations are distributed between the washing machine and the dryer. What the consumer would like is to be able to dose the detergent composition and the softening composition to a single location.

Unfortunately, liquid detergent compositions tend to be incompatible with softening compositions. Liquid detergent compositions comprise anionic surfactants to help clean the clothing. Softening compositions typically comprise cationic surfactants to soften the clothing. When combined in a single package, the anionic surfactant and cationic surfactant can combine and form a solid precipitate. This results in problem with stability of the combination when packaged together in a liquid form or together in a wash liquor and a decrease in cleaning performance as compared to the detergent composition in absence of the softening composition. This incompatibility problem is among the reasons that detergent compositions and fabric softening compositions are dosed and applied separate from one another. Liquid fabric softening compositions packaged separately from detergent compositions may not be preferred by some consumers due to the inconvenience of dosing the composition to the washing machine, perceived messiness, and the texture of the product.

With these limitations in mind, there is a continuing unaddressed need for a solid form through the wash fabric softening composition that can be dispensed by the consumer together with the laundry detergent to providing softening through the wash during the washing step.

SUMMARY OF THE INVENTION

A composition comprising a plurality of particles, said particles comprising: about 25% to about 94% by weight a water soluble carrier; about 5% to about 45% by weight a quaternary ammonium compound; about 1% to about 40% by weight a fatty acid; and about 0.5% to about 10% by weight a cationic polymer; wherein each of said particles has a mass from about 1 mg to about 1 g.

DETAILED DESCRIPTION OF THE INVENTION

Figure 1:
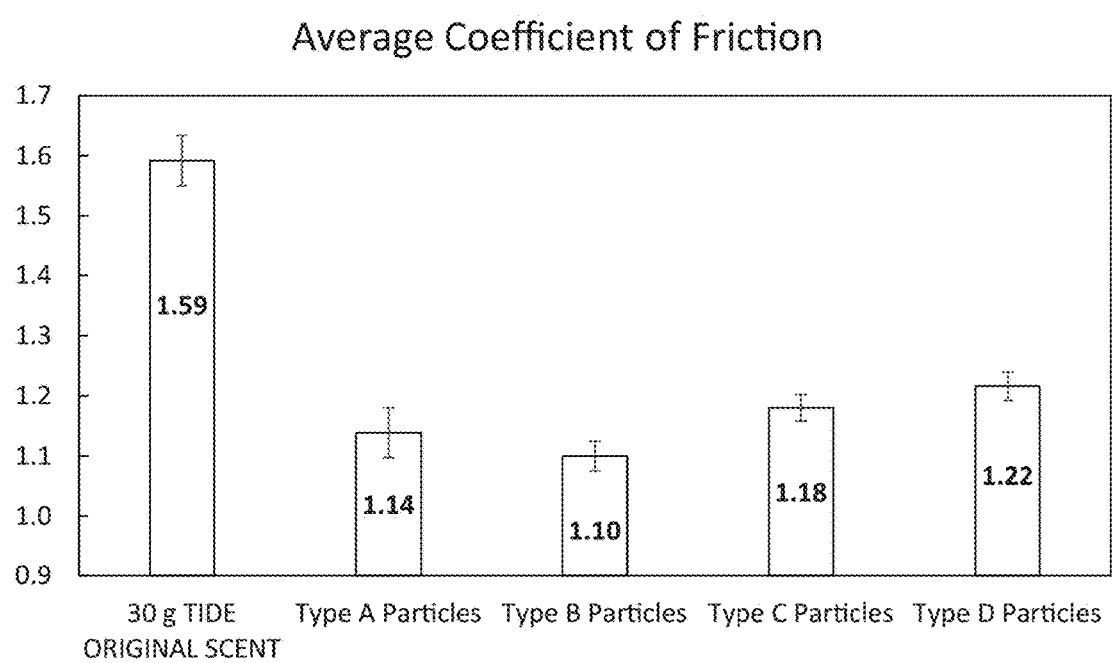
FIG. 1 is a bar chart of coefficient of friction of terries washed with detergent only and detergent combined with one of Type A-D particles.

The composition described herein can provide for a through the wash fabric softening composition that is convenient for the consumer to dose to the washing machine. The through the wash fabric softening composition can be provided in a composition comprising a plurality of particles. The particles can be provided in a package that is separate from the package of detergent composition. Having the softening composition particles in a package separate from the package of detergent composition can be beneficial since it allows the consumer to select the amount of softening composition independent of the amount of detergent composition used. This can give the consumer the opportunity to customize the amount of softening composition used and thereby the amount of softening benefit they achieve, which is a highly valuable consumer benefit.

Particulate products, especially particulates that are not dusty, are preferred by many consumers. Particulate products can be easily dosed by consumers from a package directly into the washing machine or into a dosing compartment on the washing machine. Or the consumer can dose from the package into a dosing cup that optionally provides one or more dosing indicia and then dose the particulates into a dosing compartment on the washing machine or directly to the drum. For products in which a dosing cup is employed, particulate products tend to be less messy than liquid products.

The particles of the fabric softening composition can comprise a carrier, a quaternary ammonium compound, and cationic polymer. The carrier carries the quaternary ammonium compound to the washing machine. The particle is dissolved into the wash liquor. The quaternary ammonium compound is deposited from the wash liquor onto the fibers of the fabric. And the cationic polymer is deposited onto the fibers of the fabric and promotes deposition of the quaternary ammonium compound onto the fabric. The cationic polymer and quaternary ammonium compound deposited on the fibers provides the consumer with a feeling of softness.

The particles can comprise about 25% to about 94% by weight a water soluble carrier. The particles can further comprise about 5% to about 45% by weight a quaternary ammonium compound formed from a parent fatty acid compound having an Iodine Value from about 18 to about 60, optionally from about 20 to about 60. The particles can further comprise about 0.5% to about 10% by weight a cationic polymer. Each of the particles can have a mass from about 1 mg to about 1 g. The products can have an onset of melt from about 25° C. to about 120° C. The particles can comprise clay. The particles can comprise about 0.1% to about 7% by weight clay. The clay can be bentonite.

The particles can have a ratio of percent by weight quaternary ammonium compound to percent by weight cationic polymer from about 3:1 to about 30:1, optionally from about 5:1 to about 15:1, optionally from about 5:1 to about 10:1, optionally about 8:1. Without being bound by theory, the mass fraction of quaternary ammonium compound and mass fraction of cationic polymer are balanced to achieve assistance from the cationic polymer to deposit satisfactory levels of deposition of the quaternary ammonium compound onto the fabric being treated.

The particles can have a particle Dispersion Time less than about 30 minutes, optionally less than about 28 minutes, optionally less than about 25 minutes, optionally less than about 22 minutes, optionally less than about 20 minutes, optionally from about 5 minutes to about 30 minutes, optionally from about 8 minutes to about 25 minutes, optionally from about 10 minutes to about 25 minutes. The particles can have a particle Dispersion Time from about 3 minutes to about 30 minutes, optionally from about 5 minutes to about 30 minutes, optionally from about 10 minutes to about 30 minutes. Particles having a Dispersion Time shorter than the length of the wash sub-cycle may be desirable to provide for maximum softness benefit and to reduce the potential for particles or remnants thereof to carry over into the rinse sub-cycle.

The particles can comprise less than about 10% by weight water, optionally less than about 8% by weight water, optionally less than about 5% by weight water, optionally less than about 3% by weight water. Optionally, the particles can comprise from about 0% to about 10% by weight water, optionally from about 0% to about 8% by weight water, optionally from about 0% to about 5% by weight water, optionally from about 0% to about 3% by weight water. Decreasing or having these ranges of water content are thought to provide particles that are more stable. The lower the mass fraction of water, the more stable the particles are thought to be.

Water Soluble Carrier

The particles can comprise a water soluble carrier. The water soluble carrier acts to carry the fabric care benefit agents to the wash liquor. Upon dissolution of the carrier, the fabric care benefit agents are dispersed into the wash liquor.

The water soluble carrier can be a material that is soluble in a wash liquor within a short period of time, for instance less than about 10 minutes. The water soluble carrier can be selected from the group consisting of water soluble inorganic alkali metal salt, water-soluble alkaline earth metal salt, water-soluble organic alkali metal salt, water-soluble organic alkaline earth metal salt, water soluble carbohydrate, water-soluble silicate, water soluble urea, and any combination thereof.

Alkali metal salts can be, for example, selected from the group consisting of salts of lithium, salts of sodium, and salts of potassium, and any combination thereof. Useful alkali metal salts can be, for example, selected from the group consisting of alkali metal fluorides, alkali metal chlorides, alkali metal bromides, alkali metal iodides, alkali metal sulfates, alkali metal bisulfates, alkali metal phosphates, alkali metal monohydrogen phosphates, alkali metal dihydrogen phosphates, alkali metal carbonates, alkali metal monohydrogen carbonates, alkali metal acetates, alkali metal citrates, alkali metal lactates, alkali metal pyruvates, alkali metal silicates, alkali metal ascorbates, and combinations thereof.

Alkali metal salts can be selected from the group consisting of sodium fluoride, sodium chloride, sodium bromide, sodium iodide, sodium sulfate, sodium bisulfate, sodium phosphate, sodium monohydrogen phosphate, sodium dihydrogen phosphate, sodium carbonate, sodium hydrogen carbonate, sodium acetate, sodium citrate, sodium lactate, sodium tartrate, sodium silicate, sodium ascorbate, potassium fluoride, potassium chloride, potassium bromide, potassium iodide, potassium sulfate, potassium bisulfate, potassium phosphate, potassium monohydrogen phosphate, potassium dihydrogen phosphate, potassium carbonate, potassium monohydrogen carbonate, potassium acetate, potassium citrate, potassium lactate, potassium tartrate, potassium silicate, potassium, ascorbate, and combinations thereof.

Alkaline earth metal salts can be selected from the group consisting of salts of magnesium, salts of calcium, and the like, and combinations thereof. Alkaline earth metal salts can be selected from the group consisting of alkaline metal fluorides, alkaline metal chlorides, alkaline metal bromides, alkaline metal iodides, alkaline metal sulfates, alkaline metal bisulfates, alkaline metal phosphates, alkaline metal monohydrogen phosphates, alkaline metal dihydrogen phosphates, alkaline metal carbonates, alkaline metal monohydrogen carbonates, alkaline metal acetates, alkaline metal citrates, alkaline metal lactates, alkaline metal pyruvates, alkaline metal silicates, alkaline metal ascorbates, and combinations thereof. Alkaline earth metal salts can be selected from the group consisting of magnesium fluoride, magnesium chloride, magnesium bromide, magnesium iodide, magnesium sulfate, magnesium phosphate, magnesium monohydrogen phosphate, magnesium dihydrogen phosphate, magnesium carbonate, magnesium monohydrogen carbonate, magnesium acetate, magnesium citrate, magnesium lactate, magnesium tartrate, magnesium silicate, magnesium ascorbate, calcium fluoride, calcium chloride, calcium bromide, calcium iodide, calcium sulfate, calcium phosphate, calcium monohydrogen phosphate, calcium dihydrogen phosphate, calcium carbonate, calcium monohydrogen carbonate, calcium acetate, calcium citrate, calcium lactate, calcium tartrate, calcium silicate, calcium ascorbate, and combinations thereof.

Inorganic salts, such as inorganic alkali metal salts and inorganic alkaline earth metal salts, do not contain carbon. Organic salts, such as organic alkali metal salts and organic alkaline earth metal salts, contain carbon. The organic salt can be an alkali metal salt or an alkaline earth metal salt of sorbic acid (i.e., asorbate). Sorbates can be selected from the group consisting of sodium sorbate, potassium sorbate, magnesium sorbate, calcium sorbate, and combinations thereof.

The water soluble carrier can be or comprise a material selected from the group consisting of a water-soluble inorganic alkali metal salt, a water-soluble organic alkali metal salt, a water-soluble inorganic alkaline earth metal salt, a water-soluble organic alkaline earth metal salt, a water-soluble carbohydrate, a water-soluble silicate, a water-soluble urea, and combinations thereof. The water soluble carrier can be selected from the group consisting of sodium chloride, potassium chloride, calcium chloride, magnesium chloride, sodium sulfate, potassium sulfate, magnesium sulfate, sodium carbonate, potassium carbonate, sodium hydrogen carbonate, potassium hydrogen carbonate, sodium acetate, potassium acetate, sodium citrate, potassium citrate, sodium tartrate, potassium tartrate, potassium sodium tartrate, calcium lactate, water glass, sodium silicate, potassium silicate, dextrose, fructose, galactose, isoglucose, glucose, sucrose, raffinose, isomalt, xylitol, candy sugar, coarse sugar, and combinations thereof. In one embodiment, the water soluble carrier can be sodium chloride. In one embodiment, the water soluble carrier can be table salt.

The water soluble carrier can be or comprise a material selected from the group consisting of sodium bicarbonate, sodium sulfate, sodium carbonate, sodium formate, calcium formate, sodium chloride, sucrose, maltodextrin, corn syrup solids, corn starch, wheat starch, rice starch, potato starch, tapioca starch, clay, silicate, citric acid carboxymethyl cellulose, fatty acid, fatty alcohol, glyceryl diester of hydrogenated tallow, glycerol, and combinations thereof.

The water soluble carrier can be selected from the group consisting of water soluble organic alkali metal salt, water soluble inorganic alkaline earth metal salt, water soluble organic alkaline earth metal salt, water soluble carbohydrate, water soluble silicate, water soluble urea, starch, clay, water insoluble silicate, citric acid carboxymethyl cellulose, fatty acid, fatty alcohol, glyceryl diester of hydrogenated tallow, glycerol, polyethylene glycol, and combinations thereof.

The water soluble carrier can be selected from the group consisting of disaccharides, polysaccharides, silicates, zeolites, carbonates, sulfates, citrates, and combinations thereof.

The water soluble carrier can be a water soluble polymer. Water soluble polymers can be selected from the group consisting of polyvinyl alcohols (PVA), modified PVAs; polyvinyl pyrrolidone; PVA copolymers such as PVA/polyvinyl pyrrolidone and PVA/polyvinyl amine; partially hydrolyzed polyvinyl acetate; polyalkylene oxides such as polyethylene oxide; polyethylene glycols; acrylamide; acrylic acid; cellulose, alkyl cellulosics such as methyl cellulose, ethyl cellulose and propyl cellulose; cellulose ethers; cellulose esters; cellulose amides; polyvinyl acetates; polycarboxylic acids and salts; polyaminoacids or peptides; polyamides; polyacrylamide; copolymers of maleic/acrylic acids; polysaccharides including starch, modified starch; gelatin; alginates; xyloglucans, other hemicellulosic polysaccharides including xylan, glucuronoxylan, arabinoxylan, mannan, glucomannan and galactoglucomannan; and natural gums such as pectin, xanthan, and carrageenan, locus bean, arabic, tragacanth; and combinations thereof. In one embodiment the polymer comprises polyacrylates, especially sulfonated polyacrylates and water-soluble acrylate copolymers; and alkylhydroxy cellulosics such as methylcellulose, carboxymethylcellulose sodium, modified carboxy-methylcellulose, dextrin, ethylcellulose, propylcellulose, hydroxy ethyl cellulose, hydroxypropyl methylcellulose, maltodextrin, polymethacrylates. In yet another embodiment the water soluble polymer can be selected from the group consisting of PVA; PVA copolymers; hydroxypropyl methyl cellulose (HPMC); and mixtures thereof.

The water soluble carrier can be selected from the group consisting of polyvinyl alcohol, modified polyvinyl alcohol, polyvinyl pyrrolidone, polyvinyl alcohol/polyvinyl pyrrolidone, polyvinyl alcohol/polyvinyl amine, partially hydrolyzed polyvinyl acetate, polyalkylene oxide, polyethylene glycol, acrylamide, acrylic acid, cellulose, alkyl cellulosics, methyl cellulose, ethyl cellulose, propyl cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides, starch, modified starch, gelatin, alginates, xyloglucans, hemicellulosic polysaccharides, xylan, glucuronoxylan, arabinoxylan, mannan, glucomannan, galactoglucomannan, natural gums, pectin, xanthan, carrageenan, locus bean, arabic, tragacanth, polyacrylates, sulfonated polyacrylates, water-soluble acrylate copolymers, alkylhydroxy cellulosics, methylcellulose, carboxymethylcellulose sodium, modified carboxymethylcellulose, dextrin, ethylcellulose, propylcellulose, hydroxyethyl cellulose, hydroxypropyl methylcellulose, maltodextrin, polymethacrylates, polyvinyl alcohol copolymers, hydroxypropyl methyl cellulose, and mixtures thereof.

The water soluble carrier can be an organic material. Organic carriers may provide a benefit of being readily soluble in water.

The water soluble carrier can be selected from the group consisting of polyethylene glycol, sodium acetate, sodium bicarbonate, sodium chloride, sodium silicate, polypropylene glycol polyoxoalkylene, polyethylene glycol fatty acid ester, polyethylene glycol ether, sodium sulfate, starch, and mixtures thereof.

The water soluble carrier can be polyethylene glycol (PEG). PEG can be a convenient material to employ to make particles because it can be sufficiently water soluble to dissolve during a wash cycle when the particles have the range of mass disclosed herein. Further, PEG can be easily processed as melt. The onset of melt temperature of PEG can vary as a function of molecular weight of the PEG. The particles can comprise about 25% to about 94% by weight PEG having a weight average molecular weight from about 2000 to about 13000. PEG has a relatively low cost, may be formed into many different shapes and sizes, minimizes unencapsulated perfume diffusion, and dissolves well in water. PEG comes in various weight average molecular weights. A suitable weight average molecular weight range of PEG includes from about 2,000 to about 13,000, alternatively from about 4,000 to about 13,000, alternatively from about 4,000 to about 12,000, alternatively from about 4,000 to about 11,000, alternatively from about 5,000 to about 11,000, alternatively from about 6,000 to about 10,000, alternatively from about 7,000 to about 9,000, alternatively combinations thereof. PEG is available from BASF, for example PLURIOL E 8000 (which has a weight average molecular weight of 9000 even though 8000 is in the product name), or other PLURIOL product.

The particles can comprise about 25% to about 94% by weight of the particles of PEG. Optionally, the particles can comprise from about 35% to about 94%, optionally from about 50% to about 94%, optionally combinations thereof and any whole percentages or ranges of whole percentages within any of the aforementioned ranges, of PEG by weight of the respective particles.

The carrier can comprise a material selected from the group consisting of: a polyalkylene polymer of formula H—$(C_2H_4O)_x$—$(CH(CH_3)CH_2O)_y$—$(C_2H_4O)_z$—OH wherein x is from about 50 to about 300, y is from about 20 to about 100, and z is from about 10 to about 200; a polyethylene glycol fatty acid ester of formula $(C_2H_4O)_q$—C(O)O—$(CH_2)_r$—$CH_3$ wherein q is from about 20 to about 200 and r is from about 10 to about 30; a polyethylene glycol fatty alcohol ether of formula HO—$(C_2H_4O)_s$—$(CH_2)_t$—

CH₃ wherein s is from about 30 to about 250 and t is from about 10 to about 30; and mixtures thereof. The polyalkylene polymer of formula H—(C₂H₄O)ₓ—(CH(CH₃)CH₂O)ᵧ—(C₂H₄O)_z—OH wherein x is from about 50 to about 300, y is from about 20 to about 100, and z is from about 10 to about 200, can be a block copolymer or random copolymer.

The carrier can comprise: polyethylene glycol; a polyalkylene polymer of formula H—(C₂H₄O)ₓ—(CH(CH₃)CH₂O)ᵧ—(C₂H₄O)_z—OH wherein x is from about 50 to about 300; y is from about 20 to about 100, and z is from about 10 to about 200; a polyethylene glycol fatty acid ester of formula (C₂H₄O)_q—C(O)O—(CH₂)ᵣ—CH₃ wherein q is from about 20 to about 200 and r is from about 10 to about 30; and a polyethylene glycol fatty alcohol ether of formula HO—(C₂H₄O)_s—(CH₂)_t—CH₃ wherein s is from about 30 to about 250 and t is from about 10 to about 30.

The carrier can comprise from about 20% to about 80% by weight of the particles of polyalkylene polymer of formula H—(C₂H₄O)ₓ—(CH(CH₃)CH₂O)ᵧ—(C₂H₄O)_z—OH wherein x is from about 50 to about 300; y is from about 20 to about 100, and z is from about 10 to about 200.

The carrier can comprise from about 1% to about 20% by weight of the particles polyethylene glycol fatty acid ester of formula (C₂H₄O)_q—C(O)O—(CH₂)ᵣ—CH₃ wherein q is from about 20 to about 200 and r is from about 10 to about 30.

The carrier can comprise from about 1% to about 10% by weight of the particles of polyethylene glycol fatty alcohol ether of formula HO—(C₂H₄O)_s—(CH₂)_t—CH₃ wherein s is from about 30 to about 250 and t is from about 10 to about 30.

Quaternary Ammonium Compound

The particles can comprise a quaternary ammonium compound so that the particles can provide a softening benefit to laundered fabrics through the wash, and in particular during the wash sub-cycle of a washer having wash and rinse sub-cycles. The quaternary ammonium compound (quat) can be an ester quaternary ammonium compound. Suitable quaternary ammonium compounds include but are not limited to, materials selected from the group consisting of ester quats, amide quats, imidazoline quats, alkyl quats, amidoester quats and combinations thereof. Suitable ester quats include but are not limited to, materials selected from the group consisting of monoester quats, diester quats, triester quats and combinations thereof.

Without being bound by theory, it is thought that the Dispersion Time of the particles that include a quaternary ammonium compound tends to decrease with increasing Iodine Value, recognizing that there is some variability with respect to this relationship.

The particles can comprise about 5% to about 45% by weight a quaternary ammonium compound. The quaternary ammonium compound can optionally have an Iodine Value from about 18 to about 60, optionally about 18 to about 56, optionally about 20 to about 60, optionally about 20 to about 56, optionally about 20 to about 42, and any whole numbers within the aforesaid ranges. Optionally the particles can comprise about 10% to about 40% by weight a quaternary ammonium compound, further optionally having any of the aforesaid ranges of Iodine Value. Optionally the particles can comprise about 20% to about 40% by weight a quaternary ammonium compound, further optionally having the aforesaid ranges of Iodine Value.

The quaternary ammonium compound can be selected from the group consisting of esters of bis-(2-hydroxypropyl)-dimethylammonium methylsulfate, isomers of esters of bis-(2-hydroxypropyl)-dimethylammonium methylsulfate and fatty acid, N,N-bis-(stearoyl-2-hydroxypropyl)-N,N-dimethylammonium methylsulfate, esters of bis-(2-hydroxypropyl)-dimethylammonium methylsulfate, isomers of esters of bis-(2-hydroxypropyl)-dimethylammonium methylsulfate, esters of N,N-bis(hydroxyethyl)-N,N-dimethyl ammonium chloride, N,N-bis(stearoyl-oxy-ethyl)-N,N-dimethyl ammonium chloride, esters of N,N,N-tri(2-hydroxyethyl)-N-methyl ammonium methylsulfate, N,N-bis-(palmitoyl-2-hydroxypropyl)-N,N-dimethylammoniu methylsulfate, N,N-bis-(stearoyl-2-hydroxypropyl)-N,N-dimethylammonium chloride, 1,2-di-(stearoyl-oxy)-3-trimethyl ammoniumpropane chloride, dicanoladimethylammonium chloride, di(hard)tallowdimethylammonium chloride, dicanoladimethylammonium methylsulfate, 1-methyl-1-stearoylamidoethyl-2-stearoylimidazolinium methylsulfate, imidazoline quat (no longer used by P&G): 1-tallowylamidoethyl-2-tallowylimidazoline, dipalmitoylmethylhydroxyethylammonium methylsulfate, dipalmylmethyl hydroxyethylammoinum methylsulfate, 1,2-di(acyloxy)-3-trimethylammoniopropane chloride, and mixtures thereof.

A quaternary ammonium compound can comprise compounds of the formula:

$$\{R^2_{4-m}—N^+—[X—Y—R^1]_m\}A^- \quad (1)$$

wherein:
m is 1, 2 or 3 with proviso that the value of each m is identical;
each $R^1$ is independently hydrocarbyl, or substituted hydrocarbyl group;
each $R^2$ is independently a $C_1$-$C_3$ alkyl or hydroxyalkyl group, preferably $R^2$ is selected from methyl, ethyl, propyl, hydroxyethyl, 2-hydroxypropyl, 1-methyl-2-hydroxyethyl, poly($C_{2-3}$ alkoxy), polyethoxy, benzyl;
each X is independently $(CH_2)n$, $CH_2$—$CH(CH_3)$— or CH—$(CH_3)$—$CH_2$— and
each n is independently 1, 2, 3 or 4, preferably each n is 2;
each Y is independently —O—(O)C— or —C(O)—O—;
A- is independently selected from the group consisting of chloride, methylsulfate, ethylsulfate, and sulfate, preferably A- is selected from the group consisting of chloride and methyl sulfate;
with the proviso that the sum of carbons in each $R^1$, when Y is —O—(O)C—, is from 13 to 21, preferably the sum of carbons in each $R^1$, when Y is —O—(O)C—, is from 13 to 19.

The quaternary ammonium compound can comprise compounds of the formula:

[R3N+CH2CH(YR1)(CH₂YR1)]X— wherein each Y, R, R1, and X— have the same meanings as before. Such compounds include those having the formula:

[CH₃]₃ N(+)[CH₂CH(CH2O(O)CR1)O(O)CR1] Cl(−)  (2)

wherein each R is a methyl or ethyl group and preferably each R1 is in the range of C15 to C19. As used herein, when the diester is specified, it can include the monoester that is present.

An example of a preferred DEQA (2) is the "propyl" ester quaternary ammonium fabric softener active having the formula 1,2-di(acyloxy)-3-trimethylammoniopropane chloride. A third type of preferred fabric softening active has the formula:

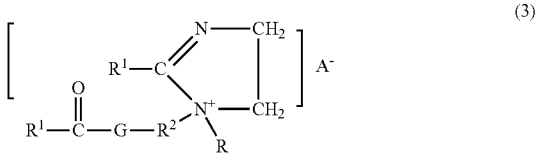

(3)

wherein each R, R1, and A- have the definitions given above; each R2 is a C1-6 alkylene group, preferably an ethylene group; and G is an oxygen atom or an —NR— group;

The quaternary ammonium compound can comprise compounds of the formula:

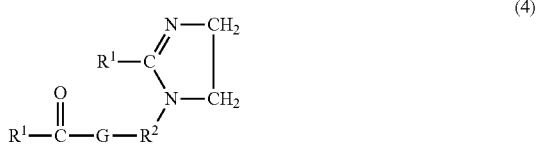

(4)

wherein R1, R2 and G are defined as above.

The quaternary ammonium compound can comprise compounds that are condensation reaction products of fatty acids with dialkylenetriamines in, e.g., a molecular ratio of about 2:1, said reaction products containing compounds of the formula:

R1-C(O)—NH—R2-NH—R3-NH—C(O)—R1    (5)

wherein R1, R2 are defined as above, and each R3 is a C1-6 alkylene group, optionally an ethylene group and wherein the reaction products may optionally be quaternized by the additional of an alkylating agent such as dimethyl sulfate.

The quaternary ammonium compound can comprise compounds of the formula:

[R1-C(O)—NR—R2-N(R)2-R3-NR—C(O)—R1]+A-    (6)

wherein R, R1, R2, R3 and A- are defined as above;

The quaternary ammonium compound can comprise compounds that are reaction products of fatty acid with hydroxyalkylalkylenediamines in a molecular ratio of about 2:1, said reaction products containing compounds of the formula:

R1-C(O)—NH—R2-N(R3OH)—C(O)—R1    (7)

wherein R1, R2 and R3 are defined as above;

A eighth type of preferred fabric softening active has the formula:

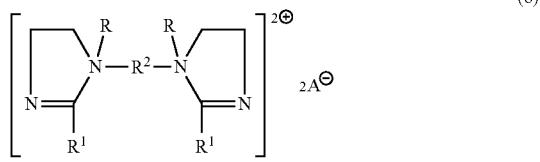

(8)

wherein R, R1, R2, and A- are defined as above.

Non-limiting examples of compound (1) are N,N-bis (stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate.

Non-limiting examples of compound (2) is 1,2 di(stearoyl-oxy) 3 trimethyl ammoniumpropane chloride.

A non-limiting example of Compound (3) is 1-methyl-1-stearoylamidoethyl-2-stearoylimidazolinium methylsulfate wherein R1 is an acyclic aliphatic C15-C17 hydrocarbon group, R2 is an ethylene group, G is a NH group, R5 is a methyl group and A- is a methyl sulfate anion, available commercially from the Witco Corporation under the trade name Varisoft®.

A non-limiting example of Compound (4) is 1-tallowylamidoethyl-2-tallowylimidazoline wherein R1 is an acyclic aliphatic C15-C17 hydrocarbon group, R2 is an ethylene group, and G is a NH group.

A non-limiting example of Compound (5) is the reaction products of fatty acids with diethylenetriamine in a molecular ratio of about 2:1, said reaction product mixture containing N,N"-dialkyldiethylenetriamine with the formula:

R1-C(O)—NH—CH2CH2-NH—CH2CH2-NH—C(O)—R1 wherein R1-C(O) is an alkyl group of a commercially available fatty acid derived from a vegetable or animal source, such as Emersol® 223LL or Emersol® 7021, available from Henkel Corporation, and R2 and R3 are divalent ethylene groups.

A non-limiting example of Compound (6) is a difatty amidoamine based softener having the formula:

[R1-C(O)—NH—CH2CH2-N(CH3)(CH2CH2OH)—CH2CH2—NH—C(O)—R1]+CH3SO4- wherein R1-C(O) is an alkyl group, available commercially from the Witco Corporation e.g. under the trade name Varisoft® 222LT.

An example of Compound (7) is the reaction products of fatty acids with N-2-hydroxyethylethylenediamine in a molecular ratio of about 2:1, said reaction product mixture containing a compound of the formula:

R1-C(O)—NH—CH2CH2-N(CH2CH2OH)—C(O)—R1 wherein R1-C(O) is an alkyl group of a commercially available fatty acid derived from a vegetable or animal source, such as Emersol® 223LL or Emersol® 7021, available from Henkel Corporation.

An example of Compound (8) is the diauaternary compound having the formula:

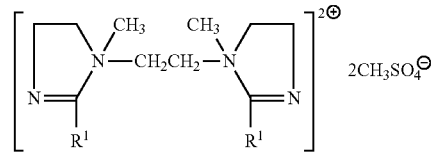

wherein R1 is derived from fatty acid, and the compound is available from Witco Company.

The quaternary ammonium compound can be di-(tallowoyloxyethyl)-N,N-methylhydroxyethylammonium methyl sulfate.

It will be understood that combinations of quaternary ammonium compounds disclosed above are suitable for use in this invention.

In the cationic nitrogenous salts herein, the anion A-, which is any softener compatible anion, provides electrical neutrality. Most often, the anion used to provide electrical neutrality in these salts is from a strong acid, especially a halide, such as chloride, bromide, or iodide. However, other anions can be used, such as methylsulfate, ethylsulfate, acetate, formate, sulfate, carbonate, and the like. Chloride and methylsulfate can be the anion A. The anion can also carry a double charge in which case A- represents half a group.

The particles can comprise from about 10 to about 40% by weight quaternary compound.

The iodine value of a quaternary ammonium compound is the iodine value of the parent fatty acid from which the compound is formed, and is defined as the number of grams of iodine which react with 100 grams of parent fatty acid from which the compound is formed.

First, the quaternary ammonium compound is hydrolysed according to the following protocol: 25 g of quaternary ammonium compound is mixed with 50 mL of water and 0.3 mL of sodium hydroxide (50% activity). This mixture is boiled for at least an hour on a hotplate while avoiding that the mixture dries out. After an hour, the mixture is allowed to cool down and the pH is adjusted to neutral (pH between 6 and 8) with sulfuric acid 25% using pH strips or a calibrated pH electrode.

Next the fatty acid is extracted from the mixture via acidified liquid-liquid extraction with hexane or petroleum ether: the sample mixture is diluted with water/ethanol (1:1) to 160 mL in an extraction cylinder, 5 grams of sodium chloride, 0.3 mL of sulfuric acid (25% activity) and 50 mL of hexane are added. The cylinder is stoppered and shaken for at least 1 minute. Next, the cylinder is left to rest until 2 layers are formed. The top layer containing the fatty acid in hexane is transferred to another recipient. The hexane is then evaporated using a hotplate leaving behind the extracted fatty acid.

Next, the iodine value of the parent fatty acid from which the fabric softening active is formed is determined following ISO3961:2013. The method for calculating the iodine value of a parent fatty acid comprises dissolving a prescribed amount (from 0.1-3 g) into 15 mL of chloroform. The dissolved parent fatty acid is then reacted with 25 mL of iodine monochloride in acetic acid solution (0.1M). To this, 20 mL of 10% potassium iodide solution and 150 mL deionised water is added. After the addition of the halogen has taken place, the excess of iodine monochloride is determined by titration with sodium thiosulphate solution (0.1M) in the presence of a blue starch indicator powder. At the same time a blank is determined with the same quantity of reagents and under the same conditions. The difference between the volume of sodium thiosulphate used in the blank and that used in the reaction with the parent fatty acid enables the iodine value to be calculated.

The quaternary ammonium compound can be that used as part of BOUNCE dryer sheets available from The Procter & Gamble Company, Cincinnati, Ohio, USA. The quaternary ammonium compound can be the reaction product of tri-ethanolamine and partially hydrogenated tallow fatty acids quaternized with dimethyl sulfate.

Cationic Polymer

The particles can comprise a cationic polymer. Cationic polymers can provide the benefit of a deposition aid that helps to deposit onto the fabric quaternary ammonium compound and possibly some other benefit agents that are contained in the particles.

The particles can comprise about 0.5% to about 10% by weight cationic polymer. Optionally, the particles can comprise about 0.5% to about 5% by weight cationic polymer, or even about 1% to about 5% by weight, or even about 2% to about 4% by weight cationic polymer, or even about 3% by weight cationic polymer. Without being bound by theory, it is thought that the cleaning performance of laundry detergent in the wash decreases with increasing levels of cationic polymer in the particles and acceptable cleaning performance of the detergent can be maintained within the aforesaid ranges.

The cationic polymer can have a cationic charge density more than about 0.05 meq/g (meq meaning milliequivalents), to 23 meq/g, preferably from about 0.1 meq/g to about 4 meq/g. even more preferably from about 0.1 meq/g to about 2 meq/g and most preferably from 0.1 meq/g to about 1 meq/g.

The above referenced cationic charge densities can be at the pH of intended use, which can be a pH from about 3 to about 9, optionally about 4 to about 9.

Cationic charge density of a polymer refers to the ratio of the number of positive charges on the polymer to the molecular weight of the polymer. Charge density is calculated by dividing the number of net charges per repeating unit by the molecular weight of the repeating unit. The positive charges may be located on the backbone of the polymers and/or the side chains of polymers. The average molecular weight of such suitable cationic polymers can generally be between about 10,000 and about 10 million, or even between about 50,000 and about 5 million, or even between about 100,000 and about 3 million.

Non-limiting examples of cationic polymers are cationic or amphoteric, polysaccharides, proteins and synthetic polymers. Cationic polysaccharides include cationic cellulose derivatives, cationic guar gum derivatives, chitosan and its derivatives and cationic starches. Cationic polysaccharides have a molecular weight from about 1,000 to about 2 million, preferably from about 100,000 to about 800,000. Suitable cationic polysaccharides include cationic cellulose ethers, particularly cationic hydroxyethylcellulose and cationic hydroxypropylcellulose. Particularly preferred are cationic cellulosic polymers with substituted anhydroglucose units that correspond to the general Structural Formula as follows:

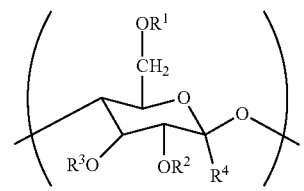

Wherein $R^1$, $R^2$ $R^3$ are each independently selected from H, $CH_3$, $C_{8-24}$ alkyl (linear or branched),

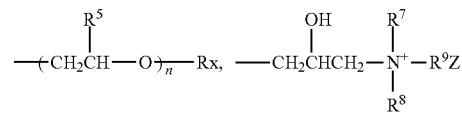

or mixtures thereof;

$R^4$ is H, n is from about 1 to about 10;

Rx is selected from the group consisting of H, $CH_3$, $C_{8-24}$ alkyl (linear or branched),

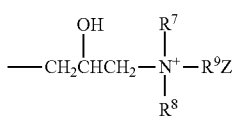

or mixtures thereof, wherein Z is a water soluble anion, preferably a chlorine ion and/or a bromine ion; $R^5$ is H, $CH_3$, $CH_2CH_3$, or mixtures thereof; $R^7$ is $CH_3$, $CH_2CH_3$, a phenyl group, a $C_{8-24}$ alkyl group (linear or branched), or mixture thereof; and $R^8$ and $R^9$ are each independently $CH_3$, $CH_2CH_3$, phenyl, or mixtures thereof:

With the provision that at least one of $R^1$, $R^2$, $R^3$ groups per anhydroglucose unit is

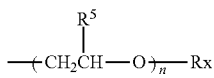

and each polymer has at least one

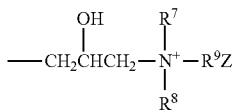

group.

The charge density of the cationic celluloses herein (as defined by the number of cationic charges per 100 anhydroglucose units) is preferably from about 0.5% to about 60%, more preferably from about 1% to about 20%, and most preferably from about 2% to about 10%.

Alkyl substitution on the anhydroglucose rings of the polymer ranges from about 0.01% to 5% per glucose unit, more preferably from about 0.05% to 2% per glucose unit, of the polymeric material.

The cationic cellulose may lightly cross-linked with a dialdehyde such as glyoxyl to prevent forming lumps, nodules or other agglomerations when added to water at ambient temperatures.

Examples of cationic hydroxyalkyl cellulose include those with the INCI name Polyquaternium 10 such as those sold under the trade names Ucare Polymer JR 30M, JR 400, JR 125, LR 400 and LK 400, Polymer PK polymers; Polyquaternium 67 such as those sold under the trade name Softcat SK TM, all of which are marketed by Dow Chemicals, Midlad MI, and Polyquaternium 4 such as those sold under the trade name Celquat H200 and Celquat L-200 available from National Starch and Chemical Company, Bridgewater, N.J. Other suitable polysaccharides include Hydroxyethyl cellulose or hydoxypropylcellulose quaternized with glycidyl $C_{12}$-$C_{22}$ alkyl dimethyl ammonium chloride. Examples of such polysaccharides include the polymers with the INCI names Polyquaternium 24 such as those sold under the trade name Quaternium LM 200 by Dow Chemicals of Midland, Mich. Cationic starches refer to starch that has been chemically modified to provide the starch with a net positive charge in aqueous solution at pH 3. This chemical modification includes, but is not limited to, the addition of amino and/or ammonium group(s) into the starch molecules. Non-limiting examples of these ammonium groups may include substituents such as trimethylhydroxypropyl ammonium chloride, dimethylstearylhydroxypropyl ammonium chloride, or dimethyldodecylhydroxypropyl ammonium chloride. The source of starch before chemical modification can be chosen from a variety of sources including tubers, legumes, cereal, and grains. Non-limiting examples of this source of starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof. Nonlimiting examples of cationic starches include cationic maize starch, cationic tapioca, cationic potato starch, or mixtures thereof. The cationic starches may comprise amylase, amylopectin, or maltodextrin. The cationic starch may comprise one or more additional modifications. For example, these modifications may include cross-linking, stabilization reactions, phophorylations, hydrolyzations, cross-linking. Stabilization reactions may include alkylation and esterification. Suitable cationic starches for use in the present compositions are commercially-available from Cerestar under the trade name C*BOND® and from National Starch and Chemical Company under the trade name CATO® 2A. Cationic galactomannans include cationic guar gums or cationic locust bean gum. An example of a cationic guar gum is a quaternary ammonium derivative of Hydroxypropyl Guar such as those sold under the trade name Jaguar C13 and Jaguar Excel available from Rhodia, Inc of Cranbury N.J. and N-Hance by Aqualon, Wilmington, Del.

Other suitable cationic polymers for use in the particles include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition used to form the particles or are soluble in a complex coacervate phase in the composition from which the particles are formed. Suitable cationic polymers are described in U.S. Pat. Nos. 3,962,418; 3,958,581; and U.S. Publication No. 2007/0207109A1.

One group of suitable cationic polymers includes those produced by polymerization of ethylenically unsaturated monomers using a suitable initiator or catalyst, such as those disclosed in WO 00/56849 and U.S. Pat. No. 6,642,200. Suitable cationic polymers may be selected from the group consisting synthetic polymers made by polymerizing one or more cationic monomers selected from the group consisting of N,N-dialkylaminoalkyl acrylate, N,N-dialkylaminoalkyl methacrylate, N,N-dialkylaminoalkyl acrylamide, N,N-dialkylaminoalkylmethacrylamide, quaternized N,N dialkylaminoalkyl acrylate quaternized N,N-dialkylaminoalkyl methacrylate, quaternized N,N-dialkylaminoalkyl acrylamide, quaternized N,N-dialkylaminoalkylmethacrylamide, Methacryloamidopropyl-pentamethyl-1,3-propylene-2-ol-ammonium dichloride, N,N,N,N',N',N'',N''-heptamethyl-N''-3-(1-oxo-2-methyl-2-propenyl)aminopropyl-9-oxo-8-azo-decane-1,4,10-triammonium trichloride, vinylamine and its derivatives, allylamine and its derivatives, vinyl imidazole, quaternized vinyl imidazole and diallyl dialkyl ammonium chloride and combinations thereof, and optionally a second monomer selected from the group consisting of acrylamide, N,N-dialkyl acrylamide, methacrylamide, N,N-dialkylmethacrylamide, $C_1$-$C_{12}$ alkyl acrylate, $C_1$-$C_{12}$ hydroxyalkyl acrylate, polyalkylene glyol acrylate, $C_1$-$C_{12}$ alkyl methacrylate, $C_1$-$C_{12}$ hydroxyalkyl methacrylate, polyalkylene glycol methacrylate, vinyl acetate, vinyl alcohol, vinyl formamide, vinyl acetamide, vinyl alkyl ether, vinyl pyridine, vinyl pyrrolidone, vinyl imidazole, vinyl caprolactam, and derivatives, acrylic acid, methacrylic acid, maleic acid, vinyl sulfonic acid, styrene sulfonic acid, acrylamidopropylmethane sulfonic acid (AMPS) and their salts. The polymer may optionally be branched or cross-linked by using branching and crosslinking monomers. Branching and crosslinking monomers include ethylene glycoldiacrylate divinylbenzene, and butadiene. A suitable polyethyleneinine useful herein is that sold under the tradename Lupasol® by BASF, AG, Lugwigschaefen, Germany In another aspect, the cationic polymer may be selected from the group consisting of cationic polysaccharide, polyethylene imine and its derivatives, poly(acrylamide-co-diallyldimethylammonium chloride), poly(acrylamide-methacrylamidopropyltrimethyl ammonium chloride), poly(acrylamide-co-N,N-dimethyl aminoethyl acrylate) and its quaternized derivatives, poly(acrylamide-co-N,N-dimethyl aminoethyl methacrylate) and its quaternized derivative, poly(hydroxyethylacrylate-co-dimethyl aminoethyl methacrylate), poly(hydroxpropylacrylate-co-dimethyl aminoethyl methacrylate), poly(hydroxpropylacrylate-co-methacrylamidopropyltrimethylammonium chloride), poly(acrylamide-co-diallyldimethyl-ammonium chloride-co-acrylic acid), poly(acrylamide-methacrylamidopropyltrimethyl ammonium chloride-co-acrylic acid), poly(diallyldimethyl ammonium chloride), poly(vinylpyrrolidone-co-dimethylaminoethyl methacrylate), poly(ethyl methacrylate-co-quaternized dimethylaminoethyl methacrylate), poly(ethyl methacrylate-co-oleyl methacrylate-co-diethylaminoethyl methacrylate), poly(diallyldimethylammonium chloride-co-acrylic acid), poly(vinyl pyrrolidone-co-quaternized vinyl imidazole) and poly(acrylamide-co-Methacryloamidopropyl-pentamethyl-1,3-propylene-2-ol-ammonium dichloride), Suitable cationic polymers include Polyquaternium-1, Polyquaternium-5, Polyquaternium-6, Polyquaternium-7, Polyquaternium-8, Polyquaternium-10, Polyquaternium-11, Polyquaternium-14, Polyquaternium-22, Polyquaternium-28, Polyquaternium-30, Polyquaternium-32 and Polyquaternium-33, as named under the International Nomenclature for Cosmetic Ingredients.

In another aspect, the cationic polymer may comprise polyethyleneimine or a polyethyleneimine derivative. In another aspect, the cationic polymer may comprise a cationic acrylic based polymer. In a further aspect, the cationic polymer may comprise a cationic polyacrylamide. In another aspect, the cationic polymer may comprise a polymer comprising polyacrylamide and polymethacrylamidoproply trimethylammonium cation. In another aspect, the cationic polymer may comprise poly(acrylamide- N-dimethyl aminoethyl acrylate) and its quaternized derivatives. In this aspect, the cationic polymer may be that sold under the tradename SEDIPUR, available from BTC Specialty Chemicals, a BASF Group, Florham Park, N.J. In a yet further aspect, the cationic polymer may comprise poly(acrylamide-co-methacrylamidopropyltrimethyl ammonium chloride). In another aspect, the cationic polymer may comprise a non-acrylamide based polymer, such as that sold under the tradename RHEOVIS CDE, available from Ciba Specialty Chemicals, a BASF group, Florham Park, N.J., or as disclosed in USPA 2006/0252668.

In another aspect, the cationic polymer may be selected from the group consisting of cationic polysaccharides. In one aspect, the cationic polymer may be selected from the group consisting of cationic cellulose ethers, cationic galactomanan, cationic guar gum, cationic starch, and combinations thereof.

Another group of suitable cationic polymers may include alkylamine-epichlorohydrin polymers which are reaction products of amines and oligoamines with epicholorohydrin, for example, those polymers listed in, for example, U.S. Pat. Nos. 6,642,200 and 6,551,986. Examples include dimethylamine-epichlorohydrin-ethylenediamine, available under the trade name CARTAFIX CB, CARTAFIX TSF, available from Clariant, Basle, Switzerland.

Another group of suitable synthetic cationic polymers may include polyamidoamine-epichlorohydrin (PAE) resins of polyalkylenepolyamine with polycarboxylic acid. The most common PAE resins are the condensation products of diethylenetriamine with adipic acid followed by a subsequent reaction with epichlorohydrin. They are available from Hercules Inc. of Wilmington Del. under the trade name KYMENE from BASF AG (Ludwigshafen, Germany) under the trade name LURESIN.

The cationic polymers may contain charge neutralizing anions such that the overall polymer is neutral under ambient conditions. Non-limiting examples of suitable counter ions (in addition to anionic species generated during use) include chloride, bromide, sulfate, methylsulfate, sulfonate, methylsulfonate, carbonate, bicarbonate, formate, acetate, citrate, nitrate, and mixtures thereof.

The weight-average molecular weight of the cationic polymer may be from about 500 to about 5,000,000, or from about 1,000 to about 2,000,000, or from about 5000 to about 1,000,000 Daltons, as determined by size exclusion chromatography relative to polyethyleneoxide standards with RI detection. In one aspect, the weight-average molecular weight of the cationic polymer may be from about 100,000 to about 800,000 Daltons.

The cationic polymer can be provided in a powder form. The cationic polymer can be provided in an anhydrous state.

Fatty Acid

The particles can comprise fatty acid. The term "fatty acid" is used herein in the broadest sense to include unprotonated or protonated forms of a fatty acid. One skilled in the art will readily appreciate that the pH of an aqueous composition will dictate, in part, whether a fatty acid is protonated or unprotonated. The fatty acid may be in its unprotonated, or salt form, together with a counter ion, such as, but not limited to, calcium, magnesium, sodium, potassium, and the like. The term "free fatty acid" means a fatty acid that is not bound to another chemical moiety (covalently or otherwise).

The fatty acid may include those containing from 12 to 25, from 13 to 22, or even from 16 to 20, total carbon atoms, with the fatty moiety containing from 10 to 22, from 12 to 18, or even from 14 (mid-cut) to 18 carbon atoms.

The fatty acids may be derived from (1) an animal fat, and/or a partially hydrogenated animal fat, such as beef tallow, lard, etc.; (2) a vegetable oil, and/or a partially hydrogenated vegetable oil such as canola oil, safflower oil, peanut oil, sunflower oil, sesame seed oil, rapeseed oil, cottonseed oil, corn oil, soybean oil, tall oil, rice bran oil, palm oil, palm kernel oil, coconut oil, other tropical palm oils, linseed oil, tung oil, etc.; (3) processed and/or bodied oils, such as linseed oil or tung oil via thermal, pressure, alkali-isomerization and catalytic treatments; (4) combinations thereof, to yield saturated (e.g. stearic acid), unsaturated (e.g. oleic acid), polyunsaturated (linoleic acid), branched (e.g. isostearic acid) or cyclic (e.g. saturated or unsaturated α-disubstituted cyclopentyl or cyclohexyl derivatives of polyunsaturated acids) fatty acids.

Mixtures of fatty acids from different fat sources can be used.

The cis/trans ratio for the unsaturated fatty acids may be important, with the cis/trans ratio (of the C18:1 material) being from at least 1:1, at least 3:1, from 4:1 or even from 9:1 or higher.

Branched fatty acids such as isostearic acid are also suitable since they may be more stable with respect to oxidation and the resulting degradation of color and odor quality.

The fatty acid may have an iodine value from 0 to 140, from 50 to 120 or even from 85 to 105.

The particles can comprise from about 1% to about 40% by weight fatty acid. The fatty acid can be selected from the group consisting of, a saturated fatty acids, unsaturated fatty acid, and mixtures thereof. The fatty acid can be a blend of saturated fatty acids, a blend of unsaturated fatty acids, and mixtures thereof. The fatty acid can be substituted or unsubstituted. The fatty acid can be provided with the quaternary ammonium compound. The fatty acid can have an Iodine Value of zero.

The fatty acid can be selected from the group consisting of stearic acid, palmitic acid, coconut oil, palm kernel oil, stearic acid palmitic acid blend, oleic acid, vegetable oil, partially hydrogenated vegetable oil, and mixtures thereof.

The fatty acid can be Stearic acid CAS No. 57-11-4. The fatty acid can be palmitic acid CAS No. 57-10-3. The fatty acid can be a blend of stearic acid and coconut oil.

The fatty acid can be C12 to C22 fatty acid. C12 to C22 fatty acid can have tallow or vegetable origin, can be saturated or unsaturated, can be substituted or unsubstituted.

Without being bound by theory, fatty acid may help as a processing aid for uniformly mixing the formulation components of the particles.

Particles

The particles can have individual mass from about 1 mg to about 1 g. The smaller the particles the faster they tend to dissolve in water. The plurality of particles can have an individual or mean particle mass of from about 1 mg to about 1000 mg, alternatively from about 5 mg to about 500 mg, alternatively from about 5 mg to about 200 mg, alternatively from about 10 mg to about 100 mg, alternatively from about 20 mg to about 50 mg, alternatively from about 35 mg to about 45 mg, alternatively about 38 mg. The plurality of particles can have standard deviation of mass of less than about 30 mg, alternatively less than about 15 mg, alternatively less than about 5 mg, alternatively about 3 mg. The mean particle of mass within the aforesaid ranges can provide for a Dispersion Time in water that permits the particles to dissolve during a typical wash cycle. Without being bound by theory, it is thought that particles have such a standard deviation of mass can have a more uniform Dispersion Time in water as compared to particles having a broader standard deviation of mass. The smaller the standard deviation of mass of the particles the more uniform the Dispersion Time. The mass of the individual particles forming the plurality particles can be set to provide the desired Dispersion Time, which might be some fraction of the length of the typical washing cycle in a washing machine. Particles formed from polyethylene glycol having a weight average molecular weight of about 9000 can have mean particle mass of about 38 mg and standard deviation of mass of about 3 mg.

The plurality of particles can be substantially free from particles having a mass less than 10 mg. This can be practical for limiting the ability of the particles to become airborne.

An individual particle may have a volume from about 0.003 cm$^3$ to about 5 cm$^3$, optionally from about 0.003 cm$^3$ to about 1 cm$^3$, optionally from about 0.003 cm$^3$ to about 0.5 cm$^3$, optionally from about 0.003 cm$^3$ to about 0.2 cm$^3$, optionally from about 0.003 cm$^3$ to about 0.15 cm$^3$. Smaller particles are thought to provide for better packing of the particles in a container and faster dissolution in the wash.

The composition can comprise particles that are retained on a number 10 sieve as specified by ASTM International, ASTM E11-13. The composition can comprise particles wherein more than about 50% by weight, optionally more than about 70% by weight, optionally more than about 90% by weight, of the particles are retained on a number 10 sieve as specified by ASTM International, ASTM E11-13. It can be desirable to provide particles sized as such because particles retained on a number 10 sieve may be easier to handle than smaller particles.

The composition can comprise particles that are retained on a number 6 sieve as specified by ASTM International, ASTM E11-13. The composition can comprise particles wherein more than about 50% by weight, optionally more than about 70% by weight, optionally more than about 90% by weight, of the particles are retained on a number 6 sieve as specified by ASTM International, ASTM E11-13. It can be desirable to provide particles sized as such because particles retained on a number 6 sieve may be easier to handle than smaller particles.

The composition can comprise particles that pass a sieve having a nominal sieve opening size of 22.6 mm. The composition can comprise particles that pass a sieve having a nominal sieve opening size of 22.6 mm and are retained on a sieve having a nominal sieve opening size of 0.841 mm. Particles having a size such that they are retained on a sieve having a nominal opening size of 22.6 mm may tend to have a Dispersion Time that is too great for a common wash cycle. Particles having a size such that they pass a sieve having a nominal sieve opening size of 0.841 mm may be too small to conveniently handle. Particles having a size within the aforesaid bounds may represent an appropriate balance between Dispersion Time and ease of particle handling.

Particles having the size disclosed herein can be substantial enough so that they do not readily become airborne when poured from a container, dosing cup, or other apparatus, into a wash basin or washing machine. Further, such particles as disclosed herein might be able to be easily and accurately poured from a container into a dosing cup. So, such particles may make it easy for the consumer to control the amount of quaternary ammonium compound he or she delivers to the wash.

A plurality of particles may collectively comprise a dose for dosing to a laundry washing machine or laundry wash basin. A single dose of the particles may comprise from about 1 g to about 50 g of particles. A single dose of the particles may comprise from about 5 g to about 50 g, alternatively from about 10 g to about 45 g, alternatively from about 20 g to about 40 g, alternatively combinations thereof and any whole numbers of grams or ranges of whole numbers of grams within any of the aforementioned ranges. The individual particles forming the plurality of particles that can make up the dose can have a mass from about 1 mg to about 5000 mg, alternatively from about 1 mg to about 1000 mg, alternatively from about 5 mg to about 200 mg, alternatively from about 10 mg to about 200 mg, alternatively from about 15 mg to about 50 mg, alternatively from about 20 mg to about 50 mg, alternatively from about 35 mg to about 45 mg, alternatively about 38 mg, alternatively combinations thereof and any whole numbers or ranges of whole numbers of mg within any of the aforementioned ranges. The plurality of particles can be made up of particles having different size, shape, and/or mass. The particles in a dose can each have a maximum dimension less than about 15 mm. Each of the particles in a dose can have a maximum dimension less than about 1 cm.

The particles can comprise an antioxidant. The antioxidant can help to promote stability of the color and or odor of the particles over time between production and use. The particles can comprise from about 0.01% to about 1% by weight antioxidant, optionally from about 0.001% to about 2% by weight antioxidant, optionally from about 0.01% to about 0.1% by weight antioxidant. The antioxidant can be butylated hydroxytoluene.

The particles can have an onset of melt from about 25° C. to about 120° C., optionally about 30° C. to about 60° C., optionally about 35° C. to about 50° C., optionally about 40° C., optionally from about 40° C. to about 60° C. The onset of melt of particles is determined by the Onset of Melt Test Method. Particles having an onset of melt from about 25° C. to about 120° C., optionally from about 40° C. to about 60° C., can be practical for providing storage stability of the particles during one or more time periods including but not limited to after production, during packaging, during shipment, during storage, and during use.

The particles can comprise about 67% by weight polyethylene glycol having a weight average molecular weight of about 9000; about 24% by weight di-(tallowoyloxyethyl)-N,N-methylhydroxyethylammonium methyl sulfate; about 6% by weight fatty acid; and about 3% by weight cationic polysaccharide that is polymeric quaternary ammonium salt of hydroxyethylcellulose which has been reacted with an epoxide substituted with a trimethylammonium group. The particles can comprise about 60% by weight polyethylene glycol having a weight average molecular weight of about 9000; about 24% by weight di-(tallowoyloxyethyl)-N,N-methylhydroxyethylammonium methyl sulfate; about 6% by weight fatty acid; about 7% by weight unencapsulated perfume, and about 3% by weight cationic polysaccharide that is polymeric quaternary ammonium salt of hydroxyethylcellulose which has been reacted with an epoxide substituted with a trimethylammonium group.

The composition described herein can comprise a plurality of particles. The particles can comprise about 25% to about 94% by weight polyethylene glycol having a weight average molecular weight from about 2000 to about 13000; about 5% to about 45% by weight a quaternary ammonium compound; and about 0.5% to about 10% by weight a cationic polymer; wherein each of said particles has a mass from about 1 mg to about 1 g; and wherein said composition has a viscosity from about 1 Pa·s to about 10 Pa·s at 65° C., from about 1 Pa·s to about 5 Pa·s at 65° C., optionally from about 1.5 to about 4, optionally from about 1 Pa·s to about 3 Pa·s, optionally about 2. Compositions such as this can be conveniently processed as a melt. Further, compositions such as this may be processed on a rotoformer and yield particles that are hemispherical, compressed hemispherical, or particles having at least one substantially flat or flat surface. Such particles may have relatively high surface area to mass as compared to spherical particles. The practicality of processing melts can at least partially depend on the viscosity of the melt.

For any of the compositions described herein, it can be desirable for the compositions to have a viscosity from about 1 Pa·s to about 10 Pa·s at 65° C., from about 1 Pa·s to about 5 Pa·s at 65° C., optionally from about 1.5 to about 4, optionally from about 1 Pa·s to about 3 Pa·s, optionally about 2. Such compositions may be conveniently processed on a rotoformer and yield particles that are hemispherical, compressed hemispherical, or particles having at least one substantially flat or flat surface.

The viscosity of the particles at 65° C. can be controlled, by way of nonlimiting example, by adding a diluent to the composition. The particles can comprise a diluent. The diluent can be selected from the group consisting of perfume, dipropylene glycol, fatty acid, and combinations thereof.

The particles disclosed herein can be homogeneously structured particles or substantially homogeneously structured particles. A substantially homogenously structured particle is a particle in which the component materials forming the particle are substantially homogeneously mixed with one another. A substantially homogeneously structure particle need not be perfectly homogeneous. There may be variations in the degree of homogeneity that is within limits of mixing processes used by those skilled in the art in commercial applications to manufacture substantially homogeneously structured particles or homogeneously structured particles. The particles can have a continuous phase of carrier. Each of the particles can be a continuous phase of a mixture of the component materials forming the particle. So, for instance, if the particles comprise component materials A, B, and C, the particles can be a continuous phase of a mixture A, B, and C. The same can be said for any number of component materials forming the particles, by way of nonlimiting example, three, four, five, or more component materials.

A homogeneously structured particle is not a particle that has a core and coating, the particle being discrete from other particles having the same structure. A substantially homogeneously or homogeneously structured particle can be non-mechanically separable. That is, the component materials forming the homogeneously structured particle may not be mechanically separated, for instance by a knife or fine pick.

Homogeneously structured particles can be substantially free or free from inclusions having a size greater than about 500 μm. Homogeneously structured particles can be substantially free from or free from inclusions having a size greater than about 200 μm. Homogeneously structured particles can be substantially free from or free from inclusions having a size greater than about 100 μm. Without being bound by theory, an abundance of large inclusions may be undesirable because they might interfere with the dissolution of the particle in the wash or leave visually perceptible residue on the articles being washed.

In a substantially homogeneous particle, the constituent materials can be substantially randomly or randomly dispersed or the constituent materials can be substantially randomly or randomly dispersed in the carrier. Without being bound by theory, substantially homogeneous structured particles are thought to possibly be less capital intense to produce and the processes to produce such particles are thought to result in more uniform particles which are more acceptable to the consumer.

The particles disclosed herein, in any of the embodiments or combination disclosed, can have a shape selected from the group consisting of a sphere, hemisphere, oblate sphere, cylindrical, polyhedral, and oblate hemisphere. The particles disclosed herein can have ratio of maximum dimension to minimum dimension from about 10 to 1, optionally from about 8 to 1, optionally about 5 to 1, optionally about 3 to 1, optionally about 2 to 1. The particles disclosed herein can be shaped such that the particles are not flakes. Particles having a ratio of maximum dimension to minimum dimension greater than about 10 or that are flakes can tend to be fragile such the particles are prone to becoming dusty. The fragility of the particles tends to decrease with decreasing values of the ratio of maximum dimension to minimum dimension.

Process for Treating an Article of Clothing

The particles disclosed herein enable consumers to achieve softening through the wash, in particular the wash sub-cycle. By providing softening through the wash sub-cycle, consumers only need to dose the detergent composition and the particles to a single location, for example the wash basin, prior to or shortly after the start of the washing machine. This can be more convenient to consumers than using a liquid fabric enhancer that is separately dispensed into the wash basin after the wash sub-cycle is completed, for example prior to, during, or in between rinse cycles. For instance, in can be inconvenient for the consumer to manually dispense fabric softening composition after completion of the wash sub-cycle since the consumer must monitor progress of the sub-cycles of the washing machine, interrupt progress of the cycles of the washing machine, open the washing machine, and dispensing fabric softening composition into the wash basin. It can further be inconvenient to use auto-dispensing features of modern upright and high efficiency machines since that requires dispensing the fabric softening composition to a location other than where detergent composition is dispensed.

The process for treating an article of clothing can comprise the steps of providing an article of clothing in a washing machine. The article of clothing is contacted during the wash sub-cycle of the washing machine with a composition comprising a plurality of the particles disclosed herein. The particles can dissolve into water provided as part of the wash sub-cycle to form a liquor. The dissolution of the particles can occur during the wash sub-cycle.

The particles can comprise the constituent components at the weight fractions described herein. For example, the particles can comprise about 25% to about 94% by weight a water soluble carrier. The particles can further comprise about 5% to about 45% by weight a quaternary ammonium compound. Optionally, the Iodine Value of the parent fatty acid from which the quaternary ammonium compound is formed can be from about 18 to about 60. The particles can further comprise about 0.5% to about 10% a cationic polymer. The particles can each have an individual mass from about 1 mg to about 1 g. The particles can have an onset of melt from about 25° C. to about 120° C.

Washing machines have at least two basic sub-cycles within a cycle of operation: a wash sub-cycle and a rinse sub-cycle. The wash sub-cycle of a washing machine is the cycle on the washing machine that commences upon first filling or partially filing the wash basin with water. A main purpose of the wash sub-cycle is to remove and or loosen soil from the article of clothing and suspend that soil in the wash liquor. Typically, the wash liquor is drained at the end of the wash sub-cycle. The rinse sub-cycle of a washing machine occurs after the wash sub-cycle and has a main purpose of rinsing soil, and optionally some benefit agents provided to the wash sub-cycle from the article of clothing.

The process can optionally comprise a step of contacting the article of clothing during the wash sub-cycle with a detergent composition comprising an anionic surfactant. Most consumers provide a detergent composition to the wash basin during the wash sub-cycle. Detergent compositions can comprise anionic surfactant, and optionally other benefit agents including but not limited to perfume, bleach, brighteners, hueing dye, enzyme, and the like. During the wash sub-cycle, the benefit agents provided with the detergent composition are contacted with or applied to the article of clothing disposed in the wash basin. Typically, the benefit agents of detergent compositions are dispersed in a wash liquor of water and the benefit agents.

During the wash sub-cycle, the wash basin may be filled or at least partially filled with water. The particles can dissolve into the water to form a wash liquor comprising the components of the particles. Optionally, if a detergent composition is employed, the wash liquor can include the components of the detergent composition and the particles or dissolved particles. The particles can be placed in the wash basin of the washing machine before the article of clothing is placed in the wash basin of the washing machine. The particles can be placed in the wash basin of the washing machine after the article of clothing is placed in the wash basin of the washing machine. The particles can be placed in the wash basin prior to filling or partially filling the wash basin with water or after filling of the wash basin with water has commenced.

If a detergent composition is employed by the consumer in practicing the process of treating an article of clothing, the detergent composition and particles can be provided from separate packages. For instance, the detergent composition can be a liquid detergent composition provided from a bottle, sachet, water soluble pouch, dosing cup, dosing ball, or cartridge associated with the washing machine. The particles can be provided from a separate package, by way of non-limiting example, a carton, bottle, water soluble pouch, dosing cup, sachet, or the like. If the detergent composition is a solid form, such as a powder, water soluble fibrous substrate, water soluble sheet, water soluble film, water soluble film, water insoluble fibrous web carrying solid detergent composition, the particles can be provided with the solid form detergent composition. For instance, the particles can be provided from a container containing a mixture of the solid detergent composition and the particles. Optionally, the particles can be provided from a pouch formed of a detergent composition that is a water soluble fibrous substrate, water soluble sheet, water soluble film, water soluble film, water insoluble fibrous web carrying solid detergent composition.

Production of Particles

For a carrier that can be processed conveniently as a melt, the rotoforming process can be used. A mixture of molten carrier and the other materials constituting the particles is prepared, for instance in a batch or continuous mixing process. The molten mixture can be pumped to a rotoformer, for instance a Sandvik ROTOFORM 3000 having a 750 mm wide 10 m long belt. The rotoforming apparatus can have a rotating cylinder. The cylinder can have 2 mm diameter apertures set at a 10 mm pitch in the cross machine direction and 9.35 mm pitch in the machine direction. The cylinder can be set at approximately 3 mm above the belt. The belt speed and rotational speed of the cylinder can be set at about 10 m/min. The molten mixture can be passed through the apertures in the rotating cylinder and deposited on a moving conveyor that is provided beneath the rotating cylinder.

The molten mixture can be cooled on the moving conveyor to form a plurality of solid particles. The cooling can be provided by ambient cooling. Optionally the cooling can be provided by spraying the under-side of the conveyor with ambient temperature water or chilled water.

Once the particles are sufficiently coherent, the particles can be transferred from the conveyor to processing equipment downstream of the conveyor for further processing and or packaging.

Optionally, the particles can be provided with inclusions of a gas. Such occlusions of gas, for example air, can help the particles dissolve more quickly in the wash. Occlusions of gas can be provided, by way of nonlimiting example, by injecting gas into the molten precursor material and milling the mixture.

Particles can also be made using other approaches. For instance, granulation or press agglomeration can be appropriate. In granulation, the precursor material containing the constituent materials of the particles is compacted and homogenized by rotating mixing tools and granulated to form particles. For precursor materials that are substantially free of water, a wide variety of sizes of particles can be made.

In press agglomeration, the precursor material containing the constituent materials of the particles is compacted and plasticized under pressure and under the effect of shear forces, homogenized and then discharged from the press agglomeration machine via a forming/shaping process. Press agglomeration techniques include extrusion, roller compacting, pelleting, and tableting.

The precursor material containing the constituent materials of the particles can be delivered to a planetary roll extruder or twin screw extruder having co-rotating or contra-rotating screws. The barrel and the extrusion granulation head can be heated to the desired extrusion temperature. The precursor material containing the constituent materials of the particles can be compacted under pressure, plasticized, extruded in the form of strands through a multiple-bore extrusion die in the extruder head, and sized using a cutting blade. The bore diameter of the of extrusion header can be selected to provide for appropriately sized particles. The extruded particles can be shaped using a spheronizer to provide for particles that have a spherical shape.

Optionally, the extrusion and compression steps may be carried out in a low-pressure extruder, such as a flat die pelleting press, for example as available from Amandus Kahl, Reinbek, Germany. Optionally, the extrusion and compression steps may be carried out in a low pressure extruder, such as a BEXTRUDER, available from Hosokawa Alpine Aktiengesellschaft, Augsburg, Germany.

The particles can be made using roller compacting. In roller compacting the precursor material containing the constituent materials of the particles is introduced between two rollers and rolled under pressure between the two rollers to form a sheet of compactate. The rollers provide a high linear pressure on the precursor material. The rollers can be heated or cooled as desired, depending on the processing characteristics of the precursor material. The sheet of compactate is broken up into small pieces by cutting. The small pieces can be further shaped, for example by using a spheronizer.

Onset of Melt Test Method

Onset of melt is determined using the Onset of Melt Test Method as follows. Differential Scanning calorimetry (DSC) is used to quantify the temperature at which the onset of melt occurs for the peak melt transition of any given composition of particles to be tested. The melt temperature measurements are made using a high quality DSC instrument with accompanying software and nitrogen purge capability, such as TA Instruments' model Discovery DSC (TA Instruments Inc./Waters Corporation, New Castle, Del., U.S.A.). A calibration check is conducted using an Indium standard sample. The DSC instrument is considered suitable to conduct the test if the onset of melt temperature measured for the Indium standard sample is within the range of 156.3-157.3° C.

A plurality of particles of the test composition are examined to identify individual particles which comprise a first class of particle versus those which comprise a second class of particle, and those that comprise any additional number of classes which may be present. The process of examining a plurality of particles to achieve such class identifications may include many approaches, including the examination and comparison of individual particles by visual inspection, examination and comparison of individual particles based on chemical makeup, and by chemical testing to determine the presence or absence of quaternary ammonium compound, cationic polymer, or perfumes in the individual particles. Test compositions are to be tested on a per class basis (i.e., by physically separating individual particles according to their class, thus creating internally uniform samples wherein each sample comprises a single class of particle). These samples are used to test particles from each class separately from particles of other classes. The results measured for each class of particle are reported separately (i.e. on a per class basis).

For each class of particle present in the test composition, a uniform test sample is prepared by obtaining at least 5 g of particles, which are then pulverised via milling into powder form using an analytical milling device, such as the IKA basic analytical mill model A11 B S1 (IKA-Werke GmbH & Co. KG, Staufen im Breisgau, Germany). The milled sample is subsequently sieved through a clean stainless steel sieve with sieve mesh size openings of nominally 1 mm in diameter (e.g. number 18 mesh size). For each sample to be tested, at least two replicate samples are independently milled and measured. A sample of the milled material weighing approximately 5 mg is placed into the bottom of a hermetic aluminium DSC sample pan, and the sample is spread out to cover the base of the pan. A hermetic aluminium lid is placed on the sample pan, and the lid is sealed with a sample encapsulating press to prevent evaporation or weight loss during the measurement process. The DSC measurements are conducted relative to a reference standard. An empty aluminum DSC sample pan used as the reference standard, in order to measure the delta in heat adsorption of the sample-containing pan versus the empty reference pan.

The DSC instrument is set up to analyze samples using the following cycle configuration selections: Sample Purge Gas is nitrogen set at 50 mL/min; Sampling Interval is set at 0.1 s/point; Equilibrate is set at −20.00° C.; Isothermal Hold is set at 1 min. Data is collected during a single heating cycle using the settings: Ramp is set at 10.00° C./min to 90.00° C.; and Isothermal Hold is set at 90.00° C. for 1 min. A sealed sample pan containing a replicate test sample is carefully loaded into the instrument, as is an empty reference pan. The DSC analysis cycle specified above is conducted and the output data is assessed. The data acquired during the DSC heating cycle is typically plotted with Temperature on the X-axis (in ° C.) and Heat Flow normalized to sample weight (in W/g) on the Y-axis, such that melting points appear as downward (endothermic) peaks since they absorb energy.

A melt transition onset temperature is the temperature at which a deflection is first observed from the baseline previously established for the melt temperature of interest. The Peak Melt temperature is the specific temperature that requires the largest observed differential energy to transition the sample from a solid phase to a melt phase, during the specified DSC heating cycle. For the purpose of this invention, the Onset of Melt temperature is defined as the melt transition onset temperature for the Peak Melt temperature. Additional general information on the DSC technique may be found in the industry standard method ASTM D3418-03—Transition Temperatures of Polymers by DSC.

Using the DSC instrument software, two points are manually defined as the "Start and Stop Integration" baseline limits. The two points selected are on flat regions of the baseline to the left and right sides, respectively, of the melt transition peak detected. This defined area is then used to determine the peak temperature (T) which can be used to report the Peak Melt Temperature. The Onset of Melt temperature for the Peak Melt temperature is then identified by the instrument software.

For each class of particle in a test composition, the Onset of Melt temperature reported is the average result (in ° C.) from the replicate samples of that class of particle.

Dispersion Test Method

The Dispersion Time of particles is determined according to the following test method.

A magnetic stir bar and 500 mL of 25 C 137 parts per million hardness water are placed into a 600 mL capacity glass beaker located on top of a stir plate set at a stir speed of 400 rpm. The temperature of the water is maintained at 25° C. Five particles are added into the beaker of stirring water, and a timer is started immediately at the same time. The particles are then observed visually by eye under well-lit laboratory conditions without the aid of laboratory magnification devices, to monitor and assess the appearance and size of the particles with regard to its dispersion and disintegration. This visual assessment may require the use of a flash light or other bright light source to ensure accurate observations.

The visual assessment is conducted every 10 seconds over the 60 minute time period after the addition of the particles to the stirring water. If the dispersion of the particles results in the particles becoming visually undetectable as discrete objects, then the time point at which this first occurs is noted. If the dispersion of the particles results in a stable visual appearance after which no additional dispersion or disintegration is observed, then the time point at which this stable appearance first occurs is noted. A value of 60 min is assigned if the particles or remnants thereof are still visible at the 60 minutes time point and it appears that the particles or remnants thereof are still undergoing dispersion or disintegration immediately prior to the 60 min time point. For each composition being tested, the assessment is performed on ten samples from the composition to provide ten replicate measurements. The time values noted for the ten replicates are averaged, and this average value is reported as the Dispersion Time value determined for that composition.

Viscosity Test Method

The viscosity of a component of the consumer product composition, e.g. a hydrophobic conditioning agent or carrier material, is determined as follows.

For a given component, the viscosity reported is the viscosity value as measured by the following method, which generally represents the infinite-shear viscosity (or infinite-rate viscosity) of the component. Viscosity measurements are made with a TA Discovery HR-2 Hybrid Rheometer (TA Instruments, New Castle, Del., U.S.A.), and accompanying TRIOS software version 3.0.2.3156. The instrument is outfitted with a 40 mm stainless steel Parallel Plate (TA Instruments, cat. #511400.901), Peltier plate (TA Instruments cat. #533230.901), and Solvent Trap Cover (TA Instruments, cat. #511400.901). The calibration is done in accordance with manufacturer recommendations. A refrigerated, circulating water bath set to 25° C. is attached to the Peltier plate. The Peltier Plate temperature is set to 65° C. The temperature is monitored within the Control Panel until the instrument reaches the set temperature, then an additional 5 minutes is allowed to elapse to ensure equilibration before loading sample material onto the Peltier plate.

To load a liquid material (e.g. a hydrophobic conditioning agent), pre-melt the sample in an oven set to 70 C, and use a transfer pipette is used to transfer 2 ml of the liquid material onto the center surface of the Peltier plate. To load a non-liquid material (e.g. a carrier material), 2 grams of non-liquid material is added onto the center surface of the Peltier plate, and the sample is allowed to completely liquefy. If the loaded sample liquid contains visible bubbles, a period of 10 minutes is waited to allow the bubbles to migrate through the sample and burst, or a transfer pipette can be used to extract the bubbles. If bubbles still remain, then the sample is removed from the plate, the plate is cleaned with isopropanol wipe and the solvent is allowed to evaporate away. The sample loading procedure is then attempted again and repeated until a sample is loaded successfully without containing visible bubbles.

The parallel plate is lowered into position in several stages, with the gap distance initially set at 50 millimeters. After waiting 60 seconds with the plate at that gap distance, the parallel plate is further lowered into position with the gap distance set at 1 millimeter.

After the parallel plate is locked, any excess sample material is removed from the perimeter of the parallel plate using rubber policeman. It is important to ensure that the sample is evenly distributed around the edge of the parallel plate and there is no sample on the side or top of plate. If there is sample material on the side or top of the plate, this excess material is gently removed. The Solvent Trap Cover is carefully applied over the parallel plate.

The Instrument Procedures and Settings (IPS) used are as follows:
1) Conditioning Step (pre-condition the sample) under the "Environmental Control" label: "Temperature" is 65° C., "Inherit set point" is not selected, "Soak time" is 10.0 s, "Wait for temperature" is selected; under the "Wait for axial force" label: "Wait for axial force" is not selected; under the "Preshear options" label: "Perform preshear" is not selected; under the "Equilibration" label: "Perform equilibration" is selected, and "Duration" is 120 s.
2) Flow Peak Hold Step under the "Environmental Control" label: "Temperature is 25° C., "Inherit set point" is selected, "Soak time" is 0.0 s, "Wait for temperature" is not selected; under the "Test Parameters" label: "Duration" is 60 sec, "Shear rate" is 2.76 1/sec, "Inherent initial value" is not selected, "Number of points" is 20; under the "Controlled Rate Advanced" label: "Motor mode" is Auto; under the "Data acquisition" label: "End of Step" is Zero Torque, "Fast Sampling" and "Save image" are not selected; under the "Step termination" label: "Label checking: Enabled" is not selected, nor are "Equilibrium: Enabled" or "Step Repeat: Enabled" selected.
3) To measure the viscosity of the sample at additional temperatures, Step #1 above "Conditioning Step" is programed as the next step, and the "Temperature" is set to 60C (under the "Environmental Control"). All other parameters are kept the same.
4) Flow Peak Hold Step is repeated exactly as written in Step #2 above, for this new temperature.
5) Steps #3 and #4 are continued using the following temperatures in the Conditioning Step: 55° C., 53° C., 52° C., 51° C., 50° C., 49° C., 48° C.

After collecting the data, the data set is opened in the TRIOS software. The data points are analyzed in the following way:
In the Peak Hold tab of the data, select Peak Hold—1 (corresponding to the data obtained at 65° C.). Report the average (mean) value of the Viscosity as expressed in units of Pa·s.
If desired, repeat this analysis to obtain the average (mean) viscosity value for the additional temperatures evaluated.

The reported viscosity value of the component measured is the average (mean) viscosity from three independent viscosity measurements (i.e. three replicate sample preparations) and is expressed in units of Pa·s Particle Dissolution and Coefficient of Friction Testing Specimens of particles were prepared to determine the particle dissolution time in water. The specimens were prepared by providing polyethylene glycol having a weight average molecular weight of 9000 in a speed mix cup (Max 100 SPEEDMIX Cup) and placing the cup of material in an oven having a temperature of 80 C overnight to melt. The speed cup of polyethylene glycol was removed from the oven in the morning and the quaternary ammonium compound and cationic hydroxyethyl cellulose were then added to the speed mix cup. The speed cup of polyethylene glycol, quaternary ammonium compound, and cationic hydroxyethyl cellulose was placed into an oven having a temperature of 80 C for four hours. The speed cup of materials was removed from the oven and placed into a SPEEDMIXER DAC 150 FVC-K (FLAK TEK Inc.) for 30 seconds at 3500 revolutions per minute. The mixture was then immediately poured onto a rubber mold that was initially at room temperature and spread with a spatula into depressions in the rubber mold. The mixture hardened in the depressions of the rubber mold to form the particles. The hardened particles were removed from the rubber mold. The mold shape was an oblate hemisphere having a diameter of 5.0 mm and a height of 2.5. Particle dissolution time testing was performed as follows. 500 mL of 25 C, 137 parts per million hardness was placed into a 600 mL beaker. A 41 mm×8 mm stir bar was placed in the beaker. The beaker was then place on a stir plate and stirred at 400 revolutions per minute. 0.4 mL of TIDE FREE detergent, available from THE PROCTER & GAMBLE COMPANY, was added and mixed for 30 seconds. Five particles, each having a mass of 38 mg +/−3 mg, were simultaneously added to the beaker and a timer was started. The time at which the mixture attained a stable visual appearance was determined by visual observation and recorded as the particle dissolution time. Globules of quaternary ammonium compound were observed upon dissolution of the particles.

For reference, a particle consisting of 100% by weight polyethylene glycol having a weight average molecular weight of 9000 had a particle dissolution time of 11 minutes.

Table 1 lists the particle dissolution time for various prepared specimens of particles. To benchmark the dissolution testing results in Table 1 in which the particles were dissolved in a solution containing detergent against the Dispersion Test Method, which does not include detergent in the solution, the Dispersion Time was measured for the series of particles under footnote 4 and the results are shown in parentheses. For that series of particles, the dissolution time in a solution containing detergent and the Dispersion Time tend to increase with increasing weight percent of quaternary ammonium compound.

TABLE 1

Particle dissolution time in a solution containing detergent composition of particles consisting of the listed weight percent of quaternary ammonium compound, 3% by weight cationic hydroxyethyl cellulose[1], and balance polyethylene glycol (note Footnote 7 regarding times reported in parentheses).

| Weight Percent of Quaternary Ammonium Compound | Particle Dissolution Time (minutes) Iodine Value of Quaternary Ammonium Compound | | | | |
|---|---|---|---|---|---|
| | 20[2] | 20[3] | —[4,7] | 42[5] | 56[6] |
| Polyethylene Glycol, Weight Average Molecular Weight = 9000 | | | | | |
| 50 | 60 | >60[a] | >60[b] (>60) | >60[b] | 38[c] |
| 45 | — | — | 50 (52) | — | — |
| 40 | 47 | >60 | 35 (40) | 60 | 50 |
| 30 | 40 | 34 | 27 (29) | 30 | 25 |
| 20 | 30 | 22 | 20 (20) | 18 | 15 |
| 10 | 15 | 17 | 16 (16) | 15 | 15 |
| Polyethylene Glycol, Weight Average Molecular Weight = 4000 | | | | | |
| 20 | 20 | 10 | — | — | 9 |
| Polyethylene Glycol, Weight Average Molecular Weight = 2000 | | | | | |
| 20 | 9 | — | — | — | — |

[1]Cationic hydroxyethyl cellulose having a weight average molecular weight of 400 kDa, a charge density of 0.18, and an average weight percent of nitrogen per anydroglucose repeat unit of 0.28% (Polymer PK available from Dow Chemical).
[2]DEEDMAC (Di-tallowoylethanolester dimethylammonium chloride), where the fatty acid moieties have an Iodine Value of ~18-22; about 20. (approximately 9% by weight ethanol and 3% by weight coconut oil).
[3]REWOQUAT DIP V 20M CONC available from EVONIK; bis-(2-hydroxypropyl)-dimethylammonium methylsulphate fatty acid ester

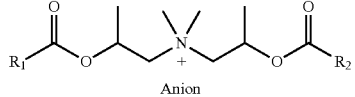

Anion wherein $R_1$ and $R_2$ is each independently a $C_{15}$-$C_{17}$, and wherein the $C_{15}$-$C_{17}$ is unsaturated or saturated, branched or linear, substituted or unsubstituted.
[4]Blend of 80% by weight of material of footnote 5 and 20% by weight fatty acid having an Iodine Value of 0 (fatty acid a blend of stearic acid and palmitic acid).
[5]C18 Unsaturated DEEHMAMS (Diethyl Ester Hydroxyethyl Methyl Ammonium Methyl Sulphate) from EVONIK.
[6]DEEDMAC (Di-tallowoylethanolester dimethylammonium chloride), where the fatty acid moieties have an Iodine Value of ~50-60; about 56. (approximately 13% by weight ethanol)
[7]Times reported in parenthesis are the Dispersion Time, measured in a solution without detergent composition in contrast to the particle dissolution time.
[a]Only about 25% dissolved after 60 minutes.
[b]Only about 50% dissolved after 60 minutes.
[c]Specimens of particles were soft that they likely would be difficult to handle, package, ship, and store.

As shown in Table 1, as the Iodine Value increases, the particle dissolution time tends to decrease. Further, the particle dissolution time tends to decrease with decreasing weight average molecular weight of polyethylene glycol. Further, the particle dissolution time tends to increase with increasing weight percent of quaternary ammonium compound. It was also observed that globules of quaternary ammonium compound tended to be smaller at lower weight fractions of quaternary ammonium compound as compared to higher weight fractions. It was further observed that globules of quaternary ammonium compound tended to be smaller for the particles comprising polyethylene glycol having a weight average molecular weight of 9000 as compared to particles comprising polyethylene glycol having a weight average molecular weight of 4000 or 2000.

Further dissolution testing was conducted to evaluate the effect of the addition of fatty acid and dipropylene glycol to the particles. The dissolution testing was performed in the same manner as that used for the compositions in Table 1.

TABLE 2

Particle dissolution time of particles consisting of the listed weight percent of quaternary ammonium compound, fatty acid, and dipropylene glycol, 3% by weight cationic hydroxyethyl cellulose having a weight average molecular weight of 400 kDa, a charge density of 0.18, and an average weight percent of nitrogen per anydroglucose repeat unit of 0.28%, and balance of polyethylene glycol having a weight average molecular weight of 9000.

| Quaternary Ammonium Compound | Particle Dissolution Time (minutes) | | |
|---|---|---|---|
| | Replicate 1 | Replicate 2 | Average |
| (Type A Particles) 30% by weight C18 Unsaturated DEEHMAMS (Diethyl Ester Hydroxyethyl Methyl Ammonium Methyl Sulphate) from EVONIK | 30 | 30 | 30 |
| (Type B Particles) 24% by weight C18 Unsaturated DEEHMAMS (Diethyl Ester Hydroxyethyl Methyl Ammonium Methyl Sulphate) from EVONIK and 6% by weight fatty acid (Iodine Value = 0) | 20 | 25 | 22 |
| (Type C Particles) 24% by weight C18 Unsaturated DEEHMAMS (Diethyl Ester Hydroxyethyl Methyl Ammonium Methyl Sulphate) from EVONIK and 6% by weight dipropylene glycol | 22 | 22 | 22 |
| (Type D Particles) 24% by weight C18 Unsaturated DEEHMAMS (Diethyl Ester Hydroxyethyl Methyl Ammonium Methyl Sulphate) from EVONIK | 22 | 22 | 22 |

As shown in Table 2, the particles having a 24% by weight of said material had a lower particle dissolution time than particles having 30% by weight said material.

The coefficient of friction of 100% terry cloth fabric washed in a liquor containing dissolved particles having the same compositions as those described in Table 2 was evaluated. For each composition, ten replicate fabrics were washed and the coefficient of friction was measured.

FIG. 1 is a graph of the average coefficient of friction for the terry cloths washed in a liquor containing 20 g of the respective dissolved particles and 50 g of TIDE ORIGINAL SCENT. Also shown are bars representing the plus minus the standard deviation.

As shown in FIG. 1, terry cloths washed in a liquor containing 50 g of TIDE ORIGINAL SCENT plus 20 g of dissolved particles that included the quaternary ammonium compound had a lower coefficient of friction compared to the coefficient of friction of the terry cloths washed in detergent only. Notably, the particles designated as Type B, which included 6% by weight fatty acid, resulted in a lower coefficient of friction than the particles designated as TYPE D, which did not include fatty acid, both types having same weight fraction of quaternary ammonium compound. And, as shown in Table 2, they Type B and Type D particles had approximately the same average particle dissolution time. So, the additional reduced coefficient of friction benefit obtained by using Type B particles over Type D particles may be achieved without a corresponding increase in particle dissolution time To evaluate the effect of viscosity of the compositions at 65° C. on particle formation, molten precursor materials of the particles was dropped onto a flat laboratory benchtop and allowed to cool. The viscosity at 65° C. of the compositions are listed in Table 3.

TABLE 3

Viscosity (Pa-s) at 65° C. of particles.

| Particles | Viscosity at 65° C. Pa-s |
|---|---|
| Type A Particles | 6.12 |
| Type B Particles | 3.92 |
| Type C Particles | 3.99 |
| Type D Particles | 5.52 |

Figure 2:
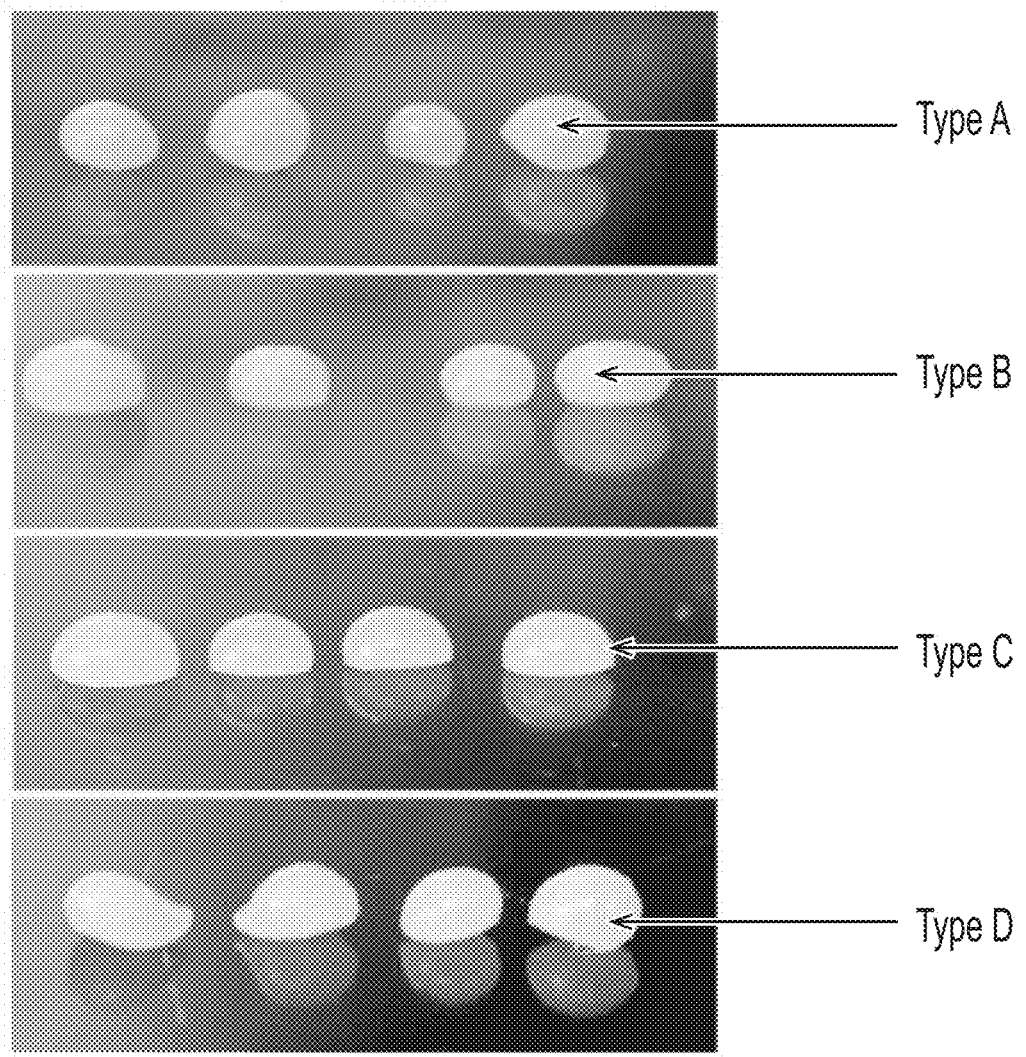
FIG. 2 is a photograph of Type A-D particles.

Photographs of the particles are shown in FIG. 2. As shown in FIG. 2, the Type B and Type C particles, which had viscosities at 65° C. of 3.92 and 3.99, respectively, the particles formed had at least one substantially flat surface. The Type A particles tended to ball up on the surface upon which they were deposited. Particles having a hemispherical or compressed hemispherical shape might have a lower Dispersion Time as compared to more rounded or chunky particles. Some of the Type D particles had protruding parts which may break off during processing, packing, shipping, shelving, transportation home, and pouring, which might result in a dust being formed from the particles.

To evaluate the effect of cationic polymer on efficacy of the particles for delivering a fabric softening benefit, the battery of tests listed in Table 4 was performed. Chinese Haier XQS75-BYD1228 washing machines were used. Each machine was set to run a Normal single cycle including a 10 minute soak period, a 14 minute wash agitation period, and 2 separate 5-minute rinses (drain and filling water for each rinse). The water used was 257 ppm hardness and 25° C. for all soak, wash, rinse steps. The water volume at each step was 30 Liters. The total fabric load weight was 1.7 kg (which includes 10 test fabric hand towel terry cloths, and the remaining ballast consisting of half cotton fabric only and half 50/50poly-cotton blend). The detergent used was ARIEL MATIC liquid detergent from China (produced by The Procter & Gamble Company). 64 g of detergent was dosed into the wash water while the wash water was filling. After the detergent was added, 12.5 g of the particles being evaluated were also added, followed by the fabric load. After the water fill was complete, the machine entered the soak period. This was followed by the wash agitation (Normal setting), and each rinse step (with corresponding spin cycle). After the wash process was completed, the fabrics were removed. The test fabric terry cloths were line dried for 36-48 hours in a 21° C./50% relative humidity controlled room. After the test fabric terry cloths had equilibrated, the coefficient of friction of each terry was evaluated. The kinematic coefficient of friction was measured using a Thwing Albert Friction/Peel Tester FP-2250 by attaching a swatch cut from the terry cloth to a sled and dragging the sled over a portion of the remaining terry cloth at a fixed rate. The kinematic coefficient of friction data reported in Tables 4-7 were all measured using the same method and instrumentation. The average for the 10 terry cloths washed in the respective product are reported in Table 4.

TABLE 4

Average coefficient of friction of terries.

| Product | Average Coefficient of Friction |
|---|---|
| ARIEL MATIC liquid detergent, 64 g | 1.42 |
| ARIEL MATIC liquid detergent, 64 g 12.8 g particles of the formula: 20% by weight quaternary ammonium compound[1]; 3% by weight cationic polymer[2]; 77% by weight polyethylene glycol having a weight average molecular weight of 9000 | 1.08 |
| ARIEL MATIC liquid detergent, 64 g 12.8 g particles of the formula: 3% by weight cationic polymer[2]; 97% by weight polyethylene glycol having a weight average molecular weight of 9000 | 1.21 |
| ARIEL MATIC liquid detergent, 64 g 12.8 g particles of the formula: 20% by weight quaternary ammonium compound[1]; 80% by weight polyethylene glycol having a weight average molecular weight of 9000 | 1.39 |

[1]DEEDMAC (Di-tallowoylethanolester dimethylammonium chloride), where the fatty acid moieties have an Iodine Value of ~18-22; e.g. 20. (approximately 9% by weight ethanol and 3% by weight coconut oil).
[2]cationic hydroxyethyl cellulose having a weight average molecular weight of 400 kDa, a charge density of 0.18, and an average weight percent of nitrogen per anydroglucose repeat unit of 0.28%.

As shown in Table 4, the terry cloths laundered with particles containing 20% by weight quaternary ammonium compound, 3% by weight cationic polymer, 77% by weight polyethylene glycol having a weight average molecular weight of 9000 had a lower coefficient of friction than the terry cloths washed in detergent alone. Further, the combination quaternary ammonium compound and cationic polymer delivered a lower coefficient of friction compared to particles without cationic polymer.

To evaluate the efficacy of various quaternary ammonium compounds for delivering a fabric softening benefit, the battery of tests listed in Table 5 was performed. North America Kenmore 80 Series top-loading washing machines were used. Each machine was set to run a Normal single cycle including a 12 minute wash agitation period, and 1 three-minute rinse. The water used was 137 ppm hardness and 25° C. for the wash, and 15.5° C. for the rinse. The water volume at each step was 64 Liters. The total fabric load weight was 3.6 kg (which includes 10 test fabric hand towel terry cloths, and the remaining ballast consisting of half cotton fabric only and half 50/50 poly-cotton blend). The detergent used was TIDE ORIGINAL SCENT liquid detergent (produced by The Procter & Gamble Company). 84.3 g of detergent was dosed into the wash water while the wash water was filling. After the detergent was added, 30.8 g of the particles being evaluated were also added, followed by the fabric load. After the water fill was complete, the machine entered the agitation period. For the DOWNY treatment, the DOWNY, available from The Procter & Gamble Company, was added into the rinse cycle as the rinse water was 2/3 filled, and the DOWNY was dosed at 48.5 g. This was followed by the wash agitation (Normal setting), and the rinse step (with corresponding spin cycle). After the wash process was completed, the fabrics were removed. The test fabrics were machine dried in Kenmore driers on Cotton/High setting, for 50 minutes. The test fabrics were then equilibrated for 24 hours in a 70 F/50% Relative Humidity controlled room. After the test fabric terry cloths had equilibrated, the coefficient of friction of each terry was evaluated. The average for the 10 terry cloths washed in the respective product are reported in Table 5.

This testing was repeated with North America Whirlpool Duet 9200 HE front-loading washing machines. Each machine was set to run a Normal single cycle including a 15 minute wash agitation period, and 2 three-minute rinse steps. The water used was 137 ppm hardness and 25° C. for the wash, and 15.5° C. for the rinse. The water volume at each step was about 19 Liters. The total fabric load weight was 3.6 kg (which includes 10 test fabric hand towel terry cloths, and the remaining ballast consisting of half cotton fabric only and half 50/50poly-cotton blend). The 30.8 g of the particles being evaluated were added with the fabric load, prior to closing the washer door and beginning the wash cycle. The detergent used was TIDE ORIGINAL SCENT HE liquid detergent (produced by The Procter & Gamble Company). 84.3 g of detergent was dosed via the detergent dispenser drawer. For the DOWNY APRIL FRESH treatment, the DOWNY APRIL FRESH, available from The Procter & Gamble Company, was added into the second rinse step via the fabric softener dispenser drawer, and the DOWNY was dosed at 48.5 g. After the wash process was completed, the fabrics were removed. The test fabrics were machine dried in Kenmore driers on Cotton/High setting, for 50 minutes. The test fabrics were then equilibrated for 24 hours in a 21° C./50% Relative Humidity controlled room. After the test fabric terry cloths had equilibrated, the coefficient of friction of each terry was evaluated. The average for the 10 terry cloths washed in the respective product are reported in Table 5.

TABLE 5

Efficacy of various quaternary ammonium compounds for delivering a fabric softening benefit.

| Product | North America Top Load Average Coefficient of Friction | North America Front Load Average Coefficient of Friction |
|---|---|---|
| TIDE ORIGINAL SCENT HE, 84.3 g | 1.55 | 1.36 |
| TIDE ORIGINAL SCENT HE, 84.3 g 30.8 g particles of the formula: 16% by weight quaternary ammonium compound[1]; 4% by weight fatty acid (Iodine Value = 0)[2] 3% by weight cationic polymer[3]; 77% by weight polyethylene glycol having a weight average molecular weight of 9000 | 1.33 | 0.99 |
| (Type B Particles from Tables 2 and 3) | 1.19 | 0.94 |
| TIDE ORIGINAL SCENT HE, 84.3 g 30.8 g particles of the formula: 24% by weight quaternary ammonium compound[1]; 6% by weight fatty acid[2]; 3% by weight cationic polymer[3]; 67% by weight polyethylene glycol having a weight average molecular weight of 9000 | | |

TABLE 5-continued

Efficacy of various quaternary ammonium compounds for delivering a fabric softening benefit.

| Product | North America Top Load Average Coefficient of Friction | North America Front Load Average Coefficient of Friction |
|---|---|---|
| TIDE ORIGINAL SCENT HE, 84.3 g 30.8 g particles of the formula: 20% by weight quaternary ammonium compound[4]; 3% by weight cationic polymer[3]; 77% by weight polyethylene glycol having a weight average molecular weight of 9000 | 1.28 | 1.01 |
| TIDE ORIGINAL SCENT HE, 84.3 g 30.8 g particles of the formula: 30% by weight quaternary ammonium compound[4]; 3% by weight cationic polymer[3]; 67% by weight polyethylene glycol having a weight average molecular weight of 9000 | 1.11 | 0.91 |
| TIDE ORIGINAL SCENT HE, 84.3 g DOWNY APRIL FRESH Liquid Fabric Softener (added to rinse), 48.5 g | 1.12 | 0.94 |

[1]C18 Unsaturated DEEHMAMS (Diethyl Ester Hydroxyethyl Methyl Ammonium Methyl Sulphate) from EVONIK.
[2]fatty acid having an Iodine Value of 0 (fatty acid a blend of stearic acid and palmitic acid).
[3]cationic hydroxyethyl cellulose having a weight average molecular weight of 400 kDa, a charge density of 0.18, and an average weight percent of nitrogen per anydroglucose repeat unit of 0.28%.
[4]REWOQUAT DIP V 20M CONC available from EVONIK; bis-(2-hydroxypropyl)-dimethylammonium methylsulphate fatty acid ester

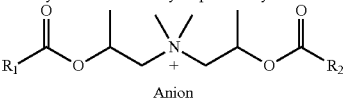

Anion wherein $R_1$ and $R_2$ is each independently a $C_{15}$-$C_{17}$, and wherein the $C_{15}$-$C_{17}$ is unsaturated or saturated, branched or linear, substituted or unsubstituted.

As shown in Table 5, for each of the particles tested under the various wash conditions, particles provided in the wash resulted in a lower average coefficient of friction of the terry cloths as compared to the treatment of using the detergent composition only. Further, and surprisingly, depending on the particular formulation of the particles and wash conditions, the particles can provide a softening benefit that is comparable to a liquid fabric softener.

To evaluate the efficacy of a synthetic cationic polymer as part of a particle formulation, the battery of tests listed in Table 6 was performed. North America Kenmore 600 Series top-loading washing machines were used. Three complete wash cycle replicates were run using the same test fabrics to evaluate the softness of the test fabrics over multiple wash cycles, according to the following details. Each machine was set to run a Normal single cycle including a 12 minute wash agitation period, and 1 three-minute rinse. The water used was 137 ppm hardness and 25° C. for the wash, and 15.5° C. for the rinse. The water volume at each step was 64 Liters. The total fabric load weight was 2.5 kg (which includes 10 test fabric hand towel terry cloths, and the remaining ballast consisting of half cotton fabric only and half 50/50poly-cotton blend). The detergent used was TIDE FREE liquid detergent (produced by The Procter & Gamble Company). 50.0 g of detergent was dosed into the wash water while the wash water was filling. After the detergent was added, 28.6 g of the particles being evaluated were also added, followed by the fabric load. After the water fill was complete, the machine entered the agitation period. This was followed by the rinse step (with corresponding spin cycle). After the entire wash process was completed, the fabrics were removed. The test fabrics were machine dried in Kenmore driers on Cotton/High setting, for 50 minutes. (The wash and dry cycles were repeated with the same test fabrics twice more before continuing to the next step.) The test fabrics were then equilibrated for 24 hours in a 21° C./50% Relative Humidity controlled room. After the test fabric terry cloths had equilibrated, the coefficient of friction of each terry was evaluated. The average for the 10 terry cloths washed in the respective product are reported in Table 6.

TABLE 6

Effect of synthetic cationic polymer on fabric softness.

| Product | North America Top Load Average Coefficient of Friction |
|---|---|
| TIDE FREE, 50 g | 1.63 |
| Tide Free, 50 g 28.6 g particles of the formula: 17.6% by weight quaternary ammonium compound[1]; 15.4% by weight fatty acid[2]; 67% by weight polyethylene glycol having a weight average molecular weight of 9000 | 1.57 |
| TIDE FREE, 50 g 28.6 g particles of the formula: 17.6% by weight quaternary ammonium compound[1]; 15.4% by weight fatty acid[2]; 3% by weight active cationic polymer[3]; 59.68% by weight polyethylene glycol having a weight average molecular weight of 9000 | 1.20 |

[1]C18 Unsaturated DEEHMAMS (Diethyl Ester Hydroxyethyl Methyl Ammonium Methyl Sulphate) from EVONIK.
[2]fatty acid having an Iodine Value of 0 (fatty acid a blend of stearic acid and palmitic acid).
[3]synthetic cationic polymer MERQUAT 280, DADMAC/AA, available from Lubrizol, Wickliffe, Ohio, USA. 41% active.

As shown in Table 6, for each of the particles tested under the various wash conditions, particles provided in the wash resulted in a lower average coefficient of friction of the terry cloths as compared to the treatment of using the detergent composition only.

To further evaluate the efficacy of a synthetic cationic polymer as part of a particle formulation, the battery of tests listed in Table 7 was performed. North America Kenmore 600 Series top-loading washing machines were used. Three complete wash cycle replicates were run using the same test fabrics to evaluate the softness of the test fabrics over multiple wash cycles, according to the following details. Each machine was set to run a Normal single cycle including a 12 minute wash agitation period, and 1 three-minute rinse. The water used was 137 ppm hardness and 25° C. for the wash, and 15.5° C. for the rinse. The water volume at each step was 64 Liters. The total fabric load weight was 3.8 kg (which includes 10 test fabric hand towel terry cloths, and the remaining ballast consisting of half cotton fabric only and half 50/50poly-cotton blend). The detergent used was TIDE FREE liquid detergent (produced by The Procter & Gamble Company). 85 g of detergent was dosed into the wash water while the wash water was filling. After the detergent was added, 28.6 g of the particles being evaluated were also added, followed by the fabric load. After the water fill was complete, the machine entered the agitation period. This was followed by the rinse step (with corresponding spin cycle). After the entire wash process was completed, the fabrics were removed. The test fabrics were machine dried in Kenmore driers on Cotton/High setting, for 50 minutes. (The wash and dry cycles were repeated with the same test fabrics twice more before continuing to the next step.) The test fabrics were then equilibrated for 24 hours in a 21° C./50% Relative Humidity controlled room. After the test fabric terry cloths had equilibrated, the coefficient of friction of each terry was evaluated. The average for the 10 terry cloths washed in the respective product are reported in Table 7.

TABLE 7

Effect of synthetic cationic polymer on fabric softness.

| Product | North America Top Load Average Coefficient of Friction |
|---|---|
| TIDE FREE, 85 g | 1.71 |
| TIDE FREE, 85 g<br>28.6 g particles of the formula:<br>30% by weight quaternary ammonium compound[1];<br>3% by weight active cationic polymer[2]<br>62.68% by weight polyethylene glycol having a weight average molecular weight of 9000 | 1.49 |
| TIDE FREE, 85 g<br>28.6 g particles of the formula:<br>30% by weight quaternary ammonium compound[1];<br>3% by weight active cationic polymer[3];<br>67% by weight polyethylene glycol having a weight average molecular weight of 9000 | 1.24 |

[1]DEEDMAC (Di-tallowoylethanolester dimethylammonium chloride), where the fatty acid moieties have an Iodine Value of ~18-22; about 20. (approximately 9% by weight ethanol and 3% by weight coconut oil)
[2]synthetic cationic polymer MERQUAT 280, DADMAC/AA, available from Lubrizol, Wickliffe, Ohio, USA, 41% active.
[3]cationic hydroxyethyl cellulose having a weight average molecular weight of 400 kDa, a charge density of 0.18, and an average weight percent of nitrogen per anydroglucose repeat unit of 0.28%

For each of the particles tested in Table 7, particles provided in the wash resulted in a lower average coefficient of friction of the terry cloths as compared to the treatment of using the detergent composition only. Further, including the cationic polymer for the quaternary ammonium compound evaluated reduced the average coefficient of friction markedly.

Surprisingly, the softening benefits observed, manifested as reductions in coefficient of friction, can be achieved with the particles provided to the wash sub-cycle. As discussed above, providing particles through the wash can be more convenient to users as compared to delivering a separate liquid fabric softening composition through the rinse. Further, surprisingly, such softening benefits can be achieved with a minimal or acceptable negative impact on whiteness, as might be expected when a quaternary ammonium compound is delivered in the presence of an anionic surfactant containing detergent composition. As such, the particles disclosed herein can be conveniently dispensed into the washing machine before, during, or immediately after the clothes are loaded into the washing machine and before the door is closed. The particles, due to their mass may be large enough to be dispensed neatly into the drum of the washing machine. The particles also may be perceived by some consumers as being less messy that liquid fabric softeners.

Examples/Combinations

An example is below:

A. A composition comprising a plurality of particles, said particles comprising:
   about 25% to about 94% by weight a water soluble carrier;
   about 5% to about 45% by weight a quaternary ammonium compound;
   about 1% to about 40% by weight a fatty acid; and
   about 0.5% to about 10% by weight a cationic polymer;
   wherein each of said particles has a mass from about 1 mg to about 1 g.

B. The composition according to Paragraph A, wherein said quaternary ammonium compound is an ester quaternary ammonium compound.

C. The composition according to any of Paragraphs A or B, wherein said particles have an onset of melt from about 25° C. to about 120° C.

D. The composition according to any of Paragraphs A to C, wherein said particles comprise about 20% to about 40% by weight said quaternary ammonium compound.

E. The composition according to any of Paragraphs A to D, wherein said particles comprise about 1% to about 5% by weight said cationic polymer.

F. The composition according to any of Paragraphs A to E, wherein said cationic polymer is a cationic polysaccharide.

G. The composition according to any of Paragraphs A to F, wherein said water soluble carrier is selected from the group consisting of polyethylene glycol, sodium acetate, sodium bicarbonate, sodium chloride, sodium silicate, polypropylene glycol polyoxoalkylene, polyethylene glycol fatty acid ester, polyethylene glycol ether, sodium sulfate, starch, and mixtures thereof.

H. The composition according to any of Paragraphs A to G, wherein said carrier comprises polyethylene glycol having a weight average molecular weight from about 2000 to about 13000.

I. The composition according to any of Paragraphs A to H, wherein said cationic polymer is a cationic polysaccharide, wherein said cationic polysaccharide is polymeric quaternary ammonium salt of hydroxyethylcellulose which has been reacted with an epoxide substituted with a trimethylammonium group.

J. The composition according to any of Paragraphs A to I, wherein said particles are less than about 10% by weight water.

K. The composition according to any of Paragraphs A to J, wherein said particles have a Dispersion Time less than about 30 minutes.

L. The composition according to any of Paragraphs A to K, wherein said water soluble carrier is a water soluble polymer.

M. The composition according to any of Paragraphs A to L, wherein said particles further comprises a material selected from the group consisting of unencapsulated perfume, dipropylene glycol, and mixtures thereof.

N. The composition according to any of Paragraphs A to M, wherein said particles are substantially homogeneously or homogeneously structured particles.

O. The composition according to any of Paragraphs A to N, wherein said particles have a ratio of maximum dimension to minimum dimension from about 10 to 1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a plurality of particles, said particles comprising:
    about 25% to about 94% by weight a water soluble carrier;
    about 5% to about 45% by weight a quaternary ammonium compound;
    about 1% to about 40% by weight a fatty acid; and
    about 0.5% to about 10% by weight a cationic polymer;
    wherein each of said particles has a mass from about 1 mg to about 1 g.

2. The composition according to claim 1, wherein said quaternary ammonium compound is an ester quaternary ammonium compound.

3. The composition according to claim 2, wherein said particles comprise about 10% to about 40% by weight said quaternary ammonium compound.

4. The composition according to claim 3, wherein said particles comprise about 1% to about 5% by weight said cationic polymer.

5. The composition according to claim 4, wherein said cationic polymer is a cationic polysaccharide.

6. The composition according to claim 5, wherein said water soluble carrier is selected from the group consisting of polyethylene glycol, sodium acetate, sodium bicarbonate, sodium chloride, sodium silicate, polypropylene glycol polyoxoalkylene, polyethylene glycol fatty acid ester, polyethylene glycol ether, sodium sulfate, starch, and mixtures thereof.

7. The composition according to claim 6, wherein said carrier comprises polyethylene glycol having a weight average molecular weight from about 2000 to about 13000.

8. The composition according to claim 6, wherein said cationic polymer is a cationic polysaccharide, wherein said cationic polysaccharide is polymeric quaternary ammonium salt of hydroxyethylcellulose which has been reacted with an epoxide substituted with a trimethylammonium group.

9. The composition according to claim 6, wherein said particles are less than about 10% by weight water.

10. The composition according to claim 6, wherein said particles have a Dispersion Time less than about 30 minutes.

11. The composition according to claim 6, wherein said particles have an onset of melt from about 25° C. to about 120° C.

12. The composition according to claim 6, wherein said particles are substantially homogeneously structured particles.

13. The composition according to claim 1, wherein said cationic polymer is a cationic polysaccharide.

14. The composition according to claim 1, wherein said water soluble carrier is selected from the group consisting of polyethylene glycol, sodium acetate, sodium bicarbonate, sodium chloride, sodium silicate, polypropylene glycol polyoxoalkylene, polyethylene glycol fatty acid ester, polyethylene glycol ether, sodium sulfate, starch, and mixtures thereof.

15. The composition according to claim 1, wherein said cationic polymer is a cationic polysaccharide, wherein said cationic polysaccharide is polymeric quaternary ammonium salt of hydroxyethylcellulose which has been reacted with an epoxide substituted with a trimethylammonium group.

16. The composition according to claim 1, wherein said particles are less than about 10% by weight water.

17. The composition according to claim 1, wherein said water soluble carrier is a water soluble polymer.

18. The composition according to claim 1, wherein said particles further comprise a material selected from the group consisting of perfume, dipropylene glycol, and mixtures thereof.

19. The composition according to claim 1, wherein said particles are substantially homogeneously structured particles.

20. A process for treating an article of clothing comprising the steps of:
    providing an article of clothing in a washing machine; and
    contacting said article of clothing during a wash sub-cycle of said washing machine with the composition according to claim 1.

* * * * *